US008348847B2

(12) United States Patent
Vezina

(10) Patent No.: US 8,348,847 B2
(45) Date of Patent: Jan. 8, 2013

(54) SYSTEM AND METHOD FOR MANAGING A PATIENT

(75) Inventor: Daniel Vezina, Park City, UT (US)

(73) Assignee: Guardsman Scientific, Inc., Park City, UT (US)

( * ) Notice: Subject to any disclaimer, the term of this patent is extended or adjusted under 35 U.S.C. 154(b) by 625 days.

(21) Appl. No.: 12/536,247

(22) Filed: Aug. 5, 2009

(65) Prior Publication Data

US 2010/0036253 A1    Feb. 11, 2010

Related U.S. Application Data

(60) Provisional application No. 61/086,254, filed on Aug. 5, 2008, provisional application No. 61/140,767, filed on Dec. 24, 2008, provisional application No. 61/224,621, filed on Jul. 10, 2009.

(51) Int. Cl.
*A61B 6/00* (2006.01)

(52) U.S. Cl. ........................................ 600/443; 600/453

(58) Field of Classification Search .................. 600/407, 600/455, 456, 457, 459, 465, 479, 481; 607/6, 607/9, 10, 14, 23, 24, 60; 709/217, 218; 705/2, 3, 7.15, 7.22
See application file for complete search history.

(56) References Cited

U.S. PATENT DOCUMENTS

| | | | |
|---|---|---|---|
| 4,165,270 A | 8/1979 | Ost | |
| 4,305,207 A | 12/1981 | Lantz | |
| 4,343,092 A | 8/1982 | Wahl et al. | |
| 4,827,943 A | 5/1989 | Bornn et al. | |
| 4,857,836 A | 8/1989 | Soelkner | |
| 4,908,568 A | 3/1990 | Soelkner | |
| 4,947,853 A | 8/1990 | Hon | |
| 5,022,410 A | 6/1991 | Hall | |
| 5,070,880 A | 12/1991 | Gomez et al. | |
| 5,394,877 A | 3/1995 | Orr et al. | |
| 5,469,852 A | 11/1995 | Nakamura et al. | |
| 5,598,845 A | 2/1997 | Chandraratna et al. | |
| 5,634,468 A | 6/1997 | Platt et al. | |
| 5,704,352 A | 1/1998 | Tremblay et al. | |
| 5,740,804 A | 4/1998 | Cerofolini | |
| 5,771,896 A | 6/1998 | Sliwa, Jr. et al. | |

(Continued)

FOREIGN PATENT DOCUMENTS

EP    0607490    7/1994

(Continued)

OTHER PUBLICATIONS

U.S. Appl. No. 13/179,748, filed Jul. 11, 2011, Vezina.

(Continued)

*Primary Examiner* — James Kish
*Assistant Examiner* — Michael N Fisher
(74) *Attorney, Agent, or Firm* — Polsinelli Shughart PC

(57) ABSTRACT

A system for managing a patient is disclosed and can include a patient interface adapted to obtain ultrasound information about the patient, a provider interface adapted to facilitate communication between the system and a provider, and a controller in communication with the patient interface and the provider interface, the controller including a clinical management module adapted to receive the ultrasound information and to recommend a clinical management strategy based upon the ultrasound information. A method of presenting a clinical management strategy is also described including obtaining information regarding a condition of a patient, developing a determinant reflecting the condition, and presenting a user with a clinical management strategy on an output device.

22 Claims, 36 Drawing Sheets

U.S. PATENT DOCUMENTS

| | | | |
|---|---|---|---|
| 5,807,268 | A | 9/1998 | Reeves et al. |
| 5,947,961 | A | 9/1999 | Netherly |
| 6,031,383 | A | 2/2000 | Streib et al. |
| 6,124,723 | A | 9/2000 | Costello |
| 6,126,636 | A | 10/2000 | Naka |
| 6,132,371 | A | 10/2000 | Dempsey et al. |
| 6,248,101 | B1 | 6/2001 | Whitmore, III |
| 6,261,231 | B1 | 7/2001 | Damphousse et al. |
| 6,285,180 | B1 | 9/2001 | Pas |
| 6,577,893 | B1 | 6/2003 | Besson et al. |
| 6,653,825 | B2 | 11/2003 | Munniksma |
| 7,215,991 | B2 | 5/2007 | Besson et al. |
| 7,244,230 | B2 | 7/2007 | Duggirala et al. |
| 2002/0120310 | A1* | 8/2002 | Linden et al. ............ 607/60 |
| 2003/0187362 | A1 | 10/2003 | Murphy et al. |
| 2003/0220578 | A1 | 11/2003 | Ho et al. |
| 2004/0006278 | A1* | 1/2004 | Webb et al. ............ 600/483 |
| 2004/0015081 | A1 | 1/2004 | Kramer et al. |
| 2005/0157888 | A1 | 7/2005 | Yang |
| 2005/0232434 | A1 | 10/2005 | Andersen |
| 2005/0288584 | A1 | 12/2005 | McMorrow et al. |
| 2006/0030782 | A1 | 2/2006 | Shennib |
| 2006/0241464 | A1* | 10/2006 | Ohtake et al. ............ 600/457 |
| 2006/0264767 | A1 | 11/2006 | Shennib |
| 2006/0265253 | A1* | 11/2006 | Rao et al. ............ 705/3 |
| 2007/0106751 | A1* | 5/2007 | Moore ............ 709/217 |
| 2007/0260285 | A1* | 11/2007 | Libbus et al. ............ 607/9 |
| 2007/0261493 | A1 | 11/2007 | Kim |
| 2007/0276251 | A1 | 11/2007 | Orenstein et al. |
| 2007/0276270 | A1 | 11/2007 | Tran |
| 2008/0004904 | A1 | 1/2008 | Tran |
| 2008/0013747 | A1 | 1/2008 | Tran |
| 2010/0168577 | A1 | 7/2010 | Vezina |

FOREIGN PATENT DOCUMENTS

| | | |
|---|---|---|
| JP | 05337108 | 12/1993 |

OTHER PUBLICATIONS

International Search Report and Written Opinion, PCT/US2009/069474, 9 pages, Feb. 25, 2010.

Anderson G. Chronic Conditions: Making the Case for Ongoing Care. Johns Hopkins University, Baltimore, MD Nov. 2007, 77 pages.

Jencks et al. Rehospitalizations among patients in the Medicare fee-for-service program. N Engl J Med 2009;360:1418-28.

International Search Report, PCT/US2009/052850, 3 pages, Sep. 29, 2009.

Hammill BG, Curtis LH, and Bennett-Guerrero E., et al. Impact of heart failure on patients undergoing major noncardiac surgery. Anesthesiology, 2008; 108:559-567.

Pelletier AJ, Ellinor PT, Camargojr CA. Increasing US Emergency Department Visit Rates and Subsequent Hosptial Admissions for Atrial Fibrillation from 1993 to 2004. Ann Emerg Med. Jan. 2008;51(1): 58-65.

Eagle KA, Berger PB, and Calkins H, et al. ACC/AHA Guideline Update for Perioperative Cardiovascular Evaluation for Noncardiac Surgery—Executive Summary. A report of the American College of Cardiology/American Heart Associatio Task Force on Pratice Guidelines (Committe to Update the 1996 Guidelines on Perioperative Cardiovascular Evaluation for Noncardiac Surgery). *Anesth Analg*. May 2002; 94(5): 1052-64.

Devereux RB, Roman MJ, Paranicas M, Lee ET, Welty TK, Fabsitz RR, Robbins D, Rhoades ER, Rodeheffer RJ, Cowan LD, Howard BV. A population-based assessment of left ventricular systolic dysfunction in middle-aged and older adults; the Strong Heart Study. Am Heart J. Mar. 2001; 141(3): 439-46.

Devereux RB, Roman MJ, Liu JE, Welty TK, Lee ET, Rodeheffer R, Fabsitz RR, Howard B. Congestive heart failure despite normal ventricular systolic function in a population-based sample: the Strong Heart Study. Am J. Cardiol. Nov. 15, 2000; 86(10): 1090-6.

Maurer MD, Burkhoff D, Fried LP, Gottdiener J, King DL, Kitzman DW. Ventricular structure and function in hypertensive participants with heart failure and a normal ejection fraction; the Cardiovascular Health Study. J Am Coll Cardiol. Mar. 6, 2007; 49(9): 982-85.

Garrett N, Martini EM. The boomers are coming: a total cost of care model of the impact of population aging on the cost of chronic conditions in the United States. Dis Manag. Apr. 2007; 10(2): 51-60.

U.S. Census Bureau. U.S. Interim Projections by Age, Sex, Race, and Hispanic Origin. Http://www.census.gov/ipc/www/usinterimproj/ Mar. 18, 2004. Last accessed Mar. 12, 2008.

Owings MF, Kozak LJ, Ambulatory and inpatient procedures in the United States, 1996. National Center for Health Statistics. Vital Health Stat 13(139), 1998.

Redfield MM, Jacobsen SJ, Burnett JC Jr, Mahoney DW, Bailey KR, Rodeheffer RJ, Burden of systolic and diastolic ventricular dysfunction in the community: appreciating the scope of the heart failure epidemic, JAMA. 2003; 289: 194-202.

Practice Guidelines for Transesophageal Echocardiology. A report by the American Society of Anesthesiologists and the Society of Cardiovascular Anesthesiologists Task Force on Transesophageal Echocardiology. Anesthesiology. 1996:986-1006.

Standards for Basic Anesthetic Monitoring (Approved by the ASA House of Delegates on Oct. 21, 1986, and last amended on Oct. 25, 2005). Http://www.asahq.org/publicationsAndServices/standards/02.pdf last accessed Mar. 12, 2008.

Polanczyk CA, Rohde LE, Goldman L, Cook EF, Thomas EJ, Marcantonio ER, Mangione CM, Lee TH: Right heart catherization and the cardiac complications in patients undergoing noncardiac surgery: An observational study. JAMA 2001; 286:309-314.

Sandham, JD, Hull RD, Brant RF, Knox L, Pineo GF, Doig CJ, Laporta DP, Viner S, Passerini L, Devitt H, Kirby A, Jacka M: A randomized, controlled trial of the use of pulmonary-artery catheters in high-risk surgical patients. N Engl J Med.

\* cited by examiner

| | CATEGORIES | | | |
|---|---|---|---|---|
| CONTRACTILE FUNCTION | HYPERDYNAMIC | NORMAL | MODERATELY REDUCED | SEVERELY REDUCED |
| VALVULAR FUNCTION<br>MITRAL VALVE REGURGITATION<br>AORTIC VALVE REGURGITATION<br>TRICUSPIC VALVE REGURGITATION | MILD<br>MILD<br>MILD | MODERATE<br>MODERATE<br>MODERATE | SEVERE<br>SEVERE<br>SEVERE | |
| LEFT VENTRICULAR DIASTOLIC FUNCTION | NORMAL | MILDLY REDUCED | MODERATELY REDUCED | SEVERELY REDUCED |
| LEFT VENTRICULAR FILLING PRESSURE<br>INTERPRETIVE<br>CALCULATED | NORMAL<br>NUMERIC VALUE - NORMAL RANGE <30 mm Hg. | ELEVATED<br>NUMERIC VALUE - NORMAL RANGE 5-15 mm Hg. | | |
| SYSTOLIC PULMONARY ARTERY PRESSURE | NUMERIC VALUE - NORMAL RANGE <30 mm Hg. | | | |
| STENOSIS<br>MITRAL STENOSIS<br>AORTIC STENOSIS | MILD (RATIO OF 1:2) | MODERATE (RATIO OF 1:3) | SEVERE<br>SEVERE (RATIO OF 1:4) | |
| CARDIAC OUTPUT | NUMERIC VALUE - NORMAL RANGE 5-6 L/MIN | | | |

FIG.15

LEFT-SIDED CARDIAC OUTPUT
LEFT VENTRICULAR OUTFLOW TRACT VELOCITY TIME INTEGRAL (LVOT VTI)

☐ NORMAL (LVOT VTI >22CM)
☐ LOWER NORMAL (LVOT VTI = 18-22CM)
☉ MILDLY DECREASED (LVOT VTI = 15-17CM)
☐ MODERATELY DECREASED (LVOT VTI = 9-14CM)
☐ MODERATELY TO SEVERELY DECREASED (LVOT VTI = 6-9CM)
☐ SEVERELY DECREASED (LVOT VTI <6CM)

☐ NOT WELL ACQUIRED (PROBABLY NL)

143

FINAL REPORT: ELECTRONIC MEDICAL REPORT

BASELINE VITAL SIGNS
BP = 165/90 HEART RATE = 75/MIN, REGULAR SpO2-92%, ROOM AIR.

CARDIAC OUTPUT
THE LEFT-SIDED CARDIAC OUTPUT IS MILDLY REDUCED (LVOT VTI = 16CM).

FILLING PRESSURES
THE LEFT-SIDED FILLING PRESSURES ARE ELEVATED.

CONTRACTILE FUNCTIONS
THE GLOBAL LEFT VENTRICULAR CONTRACTILE FUNCTION IS NORMAL (EF = 55-70%).
THE RIGHT VENTRICULAR CONTRACTILE FUNCTION IS NORMAL.

VALVULAR STRUCTURE & FUNCTIONS
THERE IS MILD MITRAL VALVE REGURGITATION. THE AORTIC VALVE IS NORMAL.
THERE IS TRIVIAL TRICUSPID REGURGITATION.

EGAM/EGHEM INTERVENTIONS
AFTERLOAD REDUCTION PERFORMED UNTIL NORMALIZATION OF CARDIAC OUTPUT.
PRELOAD REDUCTION UNTIL NORMALIZATION OF FILLING PRESSURES.

SUMMARY
EGAM WAS PERFORMED. THE BASELINE EVALUATION SHOWED A MILDLY REDUCED CARDIAC OUTPUT AND ELEVATED FILLING PRESSURES. NORMAL CONTRACTILE AND VALVULAR FUNCTIONS. AFTERLOAD REDUCTION AND PRELOAD REDUCTION WAS PERFORMED UNTIL NORMALIZATION OF CARDIAC OUTPUT AND FILLING PRESSURES.

INTERNATIONAL CLASSIFICATION OF
DISEASES CODES SELECT CONDITIONS
IDENTIFIED BY EGAM/EGHEM

☐
☐ SYSTOLIC HEART FAILURE (428.20)
☑ DIASTOLIC HEART FAILURE (428.30)
☐ COMBINED SYST+DIAS FAILURE (428.40)
☐ VOLUME DEPLETION (440.0)
☐ FLUID OVERLOAD (441.01)
☐ HTN HEART DISEASE W/O CHF (518.5)
☐ HTN HEART DISEASE WITH CHF (642.90)
☐ ACUTE COR PULMONALE (785.50)
☑ SHOCK, UNSPECIFIED (785.50)

INTERNATIONAL CLASSIFICATION OF
DISEASES CODES SELECT CONDITIONS
IDENTIFIED BY EGAM/EGHEM

☐
☐ SHOCK, CARDIOGENIC (785.51)
☑ MITRAL VALVE DISEASE (424.0)
☐ AORTIC VALVE DISEASE (424.1)
☐ TRICUSPID VALVE DISEASE (424.2)
☐ ATRIAL FIBRILLATION (427.31)
☐ ATRIAL FLUTTER (427.32)
☐ CARDIAC ARREST (997.1)
☐ NATIVE CORONARY ARTERY DISEASE (414.01)
☑ OLD MYOCARDIAL INFARCTION (412.0)

INTERNATIONAL CLASSIFICATION OF
DISEASES CODES SELECT CONDITIONS
IDENTIFIED BY EGAM/EGHEM

☐
☐ SYNCOPE (780.2)
☑ PALPITATIONS (785.1)
☐ MURMUR (785.2)
☐ SHORTNESS OF BREATH (786.09)
☐ HYPOXIA (799.02)

FIG.30

DRG OPTIMIZATION REPORT

PATIENT IDENTIFICATION
NAME:   DATE OF BIRTH:   RECORD NUMBER;   DATE OF EGAM/EGHEM:

CARDIOVASCULAR CCS IDENTIFIED BY EGAM/EGHEM
428.30: DIASTOLIC HEART FAILURE
785.50: SHOCK, UNSPECIFIED
424.0: MITRAL VALVE DISEASE
412.0: OLD MYOCARDIAL INFARCTION
788.1: PALPITATIONS

HEALTHCARE PROVIDER NAME:
HEALTHCARE PROVIDER SIGNATURE AND DATE:

PROFESSIONAL BILLING REPORT

PATIENT IDENTIFICATION

NAME:   DATE OF BIRTH:   RECORD NUMBER;   DATE OF EGAM/EGHEM:

MEDICAL PROCEDURE PERFORMED

CPT BILLING CODE: 93306-26: 2D ECHO WITH SPECTRAL DOPPLER AND COLOR DOPPLER WAS PERFORMED

ICD CODES IDENTIFIED BY PROCEDURE 428.30: DIASTOLIC HEART FAILURE: PRIMARY CODE
785.50: SHOCK, UNSPECIFIED
424.0: MITRAL VALVE DISEASE
412.0: OLD MYOCARDIAL INFARCTION
788.1: PALPITATIONS

HEALTHCARE PROVIDER NAME:
HEALTHCARE PROVIDER SIGNATURE AND DATE: 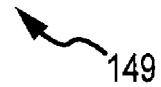
149

FIG.32

SYSTEM AND METHOD FOR MANAGING A PATIENT

CROSS REFERENCE TO RELATED CASES

The present application claims priority to U.S. Provisional Application 61/086,254, which was filed on Aug. 5, 2008, and U.S. Provisional Application 61/224,621, which was filed on Jul. 10, 2009, each entitled System (apparatus and method) to guide clinical hemodynamic management of patients requiring anesthetic care, perioperative care and critical care using cardiac ultrasound. The present application also claims priority to U.S. Provisional Application 61/140,767, which was filed on Dec. 24, 2008 and entitled Peripheral Ultrasound system (apparatus and method) for automated and uninterrupted data acquisition. The disclosures of each of the aforementioned applications are hereby incorporated by reference herein in their entireties.

FIELD OF THE INVENTION

The present disclosure relates to patient management. More particularly, the present disclosure relates to monitoring, responding to, and reporting on patient conditions. Even more particularly, the patient conditions can relate to circulatory function or hemodynamic status.

BACKGROUND

Proper circulatory function is essential to sustain and prolong life. From a more practical standpoint, circulatory function can be a factor affecting health care costs resulting from complications, hospital readmissions, and mortality. According to some professionals, ensuring the adequacy of circulatory function is one of the most important clinical goals of healthcare providers for anesthetic, perioperative, or critical care procedures. Currently, the American Society of Anesthesiology (ASA) endorses the use of the EKG monitor, systemic blood pressure (BP), pulse oximeter, and urine output (UO), known as the conventional parameters, as the basic standard of care for assessing circulatory function. However, these conventional parameters may not always provide suitable information for managing circulatory function.

Using conventional parameters may be clinically acceptable for patients with normal cardiovascular function. However, conventional parameters often provide incomplete information for patients with cardiovascular risk factors and/or comorbidities. For example, in surgical and critical care settings, managing the circulatory function of a congestive heart failure (CHF) patient with conventional parameters can lead a practitioner to deliver inappropriate amounts of intravenous (IV) fluid and/or maintain an inappropriate level of blood pressure leading to volume overload of the circulatory system of the patient. As a result of the incomplete information, many patients currently undergoing surgical procedures and/or requiring critical care medicine may not receive optimal hemodynamic management. This can lead to cardiovascular complications, hospital readmission, and/or mortality. This result is both detrimental to the health of the patient and costly to the health care system.

This weakness in the standard of care is exacerbated by the fact that CHF, with normal or reduced contractile function, is the leading admission diagnosis for medicine and cardiology services in the United States. Further adding to the problem is that diastolic dysfunction, often the underlying cause of CHF, is common among the baby boomer population. For individuals over 65, 53.8% suffer from some degree of diastolic dysfunction. (40.7% mild and 13.1% moderate or severe). The number of individuals over 65 has been projected to increase by 50% from 2000 to 2020 and as a result, the baby boomer population is recognized as a driving force for healthcare services.

Conventional circulatory function parameters may provide incomplete information for patients with cardiovascular risk factors and/or comorbidities. CHF is an example of one of those conditions and is also a common condition among the baby boomer population and the population as a whole. The health related and economic costs associated with complications, readmissions, and mortality rates need to be addressed. Accordingly, there is a need for a more capable system for managing the hemodynamics of patients.

SUMMARY

In one embodiment, a system for assisting a provider in managing a patient may include a patient interface adapted to obtain ultrasound information about the patient. The system may also include a provider interface adapted to facilitate communication between the system and the provider. The system may include a controller in communication with the patient interface and the provider interface, the controller including a clinical management module adapted to receive the ultrasound information and to recommend a clinical management strategy based upon the ultrasound information.

In another embodiment, a method of presenting a clinical management strategy for a patient may include obtaining ultrasound information regarding a condition of the patient from an ultrasound probe, communicating the ultrasound information to a controller in communication with the ultrasound probe, employing the controller to develop from the ultrasound information a determinant reflecting the condition of the patient, and providing on an output device in communication with the controller a clinical management strategy based on the determinant.

In another embodiment, a method of developing a cardiovascular determinant of a patient, may include receiving ultrasound information from a patient interface, the patient interface being adapted to obtain ultrasound information related to cardiovascular function status of the patient, processing the ultrasound information to determine the cardiovascular function status of the patient, and sending the status to a clinical management module for the development of a clinical strategy.

In another embodiment, a method of suggesting a clinical management strategy may include comparing a first order data point to a plurality of categories, where the first order data point is associated with ultrasound information, assigning a category from the plurality of categories to the first order data point based on which category of the plurality of categories, the first order data point falls, selecting a recommended intervening measure based on the assigned category, and presenting the recommended intervening measure on a display.

In another embodiment, a method of managing a patient may include positioning ultrasound probes on a patient, the ultrasound probes being in communication with a controller, using an input device to instruct the controller to obtain cardiovascular function information from the patient via the ultrasound probes, reviewing a suggested clinical management strategy, the strategy including a recommended intervening measure and being based on the cardiovascular function information, deciding whether to conduct the recommended intervening measure, a different intervening measure, or no intervening measure.

In another embodiment, a method of monitoring a patient may include monitoring a patient via ultrasound and generating information from the ultrasound. The method may also include, based upon the information, recording a clinical finding and recommending and recording an intervening measure, displaying a list of clinical findings including the clinical finding and related clinical findings, prompting a user to select from the list of clinical findings, displaying a list of intervening measures including the intervening measure and related intervening measures, prompting the user to select from the list of intervening measures, compiling a report including the selected clinical finding and the selected intervening measure.

BRIEF DESCRIPTION OF THE FIGURES

FIG. 15 is a chart showing categories for statuses of several cardiovascular determinants according to certain embodiments.

FIG. 29 is an exemplary report.

FIG. 30 is an exemplary list of an international classification of diseases for use in preparing a DRG report.

FIG. 32 is an exemplary professional billing report.

DETAILED DESCRIPTION

The present disclosure relates to a hemodynamic management system. The system can be an ultrasound based system capable of non-invasive monitoring of circulatory function including cardiac output and filling pressures. The system can be used for live monitoring of patients in a clinical setting. The system can also be used for patients undergoing anesthetic, perioperative, critical care, or other procedures and can assist in developing clinical management strategies. The live monitoring may allow providers in this setting to obtain circulatory function information previously limited to a diagnostic ultrasound setting. Access to this information in these procedural settings may allow providers to actively manage patients' circulatory function during a procedure. Moreover, the hemodynamic management may be more suitable than that which was available with the conventional parameters described above.

Figure 1:
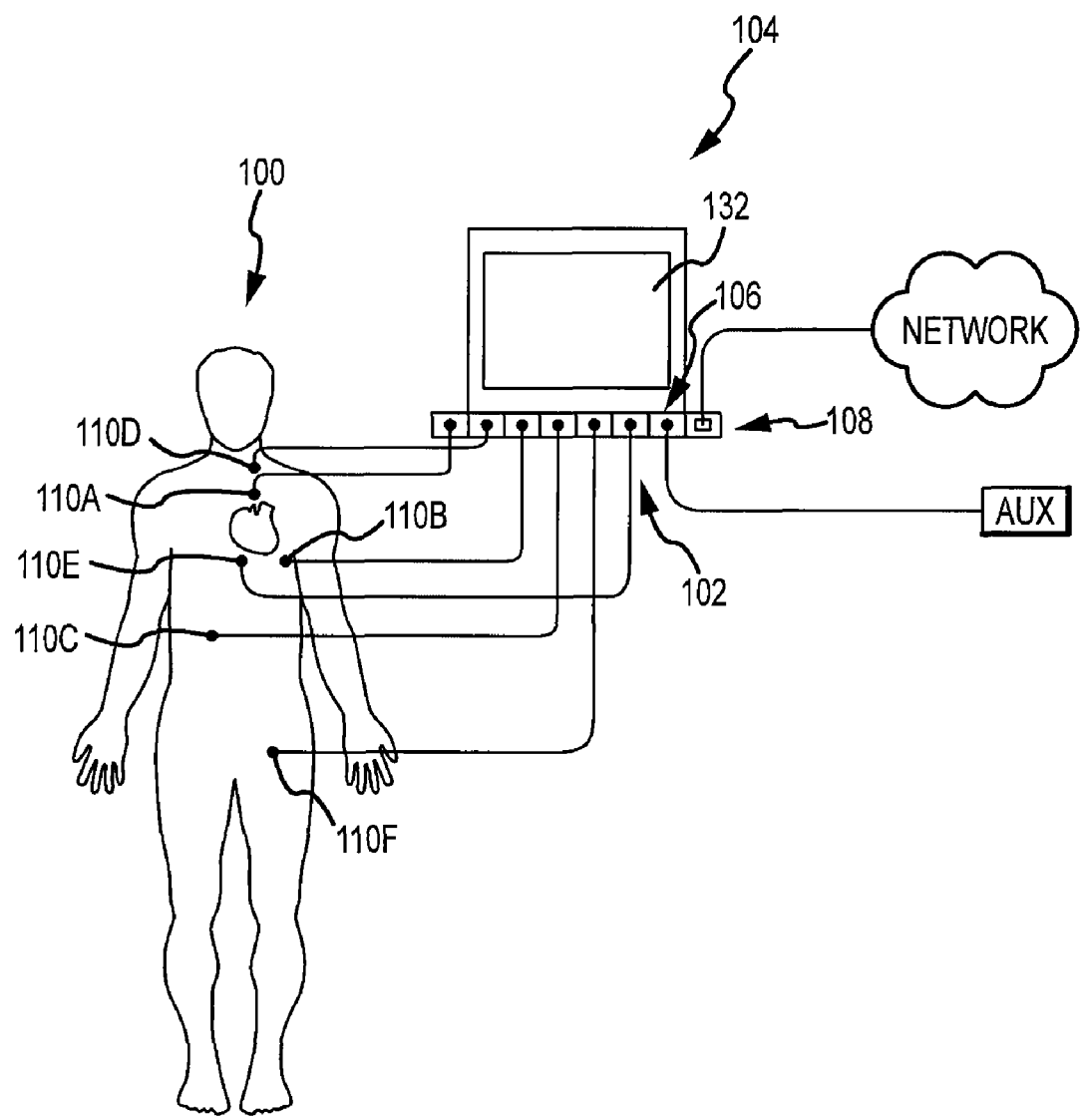
FIG. 1 shows a system for managing a patient according to certain embodiments.

Referring now to FIG. 1, a system is shown including a patient interface 100, a controller 102, a provider interface 104, an auxiliary device interface 106, and a network interface 108. The system can preferably be a hemodynamic management system where the patient interface 100 includes one or more probes 110, the controller 102 is a hemodynamic controller, and the provider interface 104 is an input and/or output device or system. The hemodynamic management system can allow the controller 102 to access circulatory information relating to a patient through the patient interface 100 and the provider interface 104 can be used to facilitate the activities of the controller 102 and to receive output information from the controller 102. In a preferred embodiment, the auxiliary device interface 106 may function to interface with devices related to conventional parameters such as an EKG or a blood pressure monitor, but other devices may also be connected through the auxiliary device interface 106. The network interface 108 can function, preferably, for use in remote supervision or quality assessment, but may be adapted for other types of network communication and data transmission.

The patient interface 100 can include one or more probes 110 adapted to be positioned on a patient and adapted to obtain information about a patient. Preferably, the probes 110 can be adapted to obtain circulatory function information about a patient. The probes 110 can be in the form of a transducer adapted to alternate between sending and receiving signals. For example, in a preferred embodiment the probes 110 can be ultrasonic transducers adapted to intermittently or continuously produce and detect ultrasonic waves.

The probes 110 can be positioned on a patient in a suitable location related to the information desired to be collected by any given probe 110. In a preferred embodiment, the probes 110 can be adapted to gather information relating to the hemodynamic status of a patient. In this embodiment, the probes 110 can be positioned in suitable locations for gathering information about the heart and may be referred to herein as cardiac probes 110. Accordingly, the probes 110 can be placed in one of several available windows. A window can be defined as a transducer location from where the heart can be imaged using ultrasound-based imaging and the windows can be external or internal to the patient's body. In a preferred embodiment, four external cardiac probes 110A-D can be provided and can be positioned in the transthoracic parasternal window, the transthoracic apical window, the sub-costal window, and the suprasternal notch window, respectively.

The transthoracic parasternal window can be defined as being located on the left side of the sternum between the $3^{rd}$ and $4^{th}$ rib. The transthoracic apical window can be defined as being located on the chest between the $5^{th}$ and $6^{th}$ left ribs posterior and lateral to the nipple line. The sub-costal window can be defined as being located under the right costal ridge and directed toward the left shoulder. The suprasternal notch window can be defined as being located at the suprasternal notch.

Preferably, an internal cardiac probe 110E can also be provided in the mid-esophageal window and thus can be positioned midway down the esophagus. In the preferred embodiment, a sixth probe 110F can be included in the form of an external non-cardiac probe 110. The sixth probe 110F can be adapted to image superficial non-cardiac structures outside the chest.

Additional or fewer probes 110 can be provided. The probes 110 can all be of the same type or they may differ and combinations of probe type or style can be included. Preferably the probes 110 can all be ultrasonic transducers. Alternatively, some of the probes 110 may include pressure, electrical signal, or temperature sensors in lieu of ultrasonic transducers and other probe types can be provided.

Figure 2:
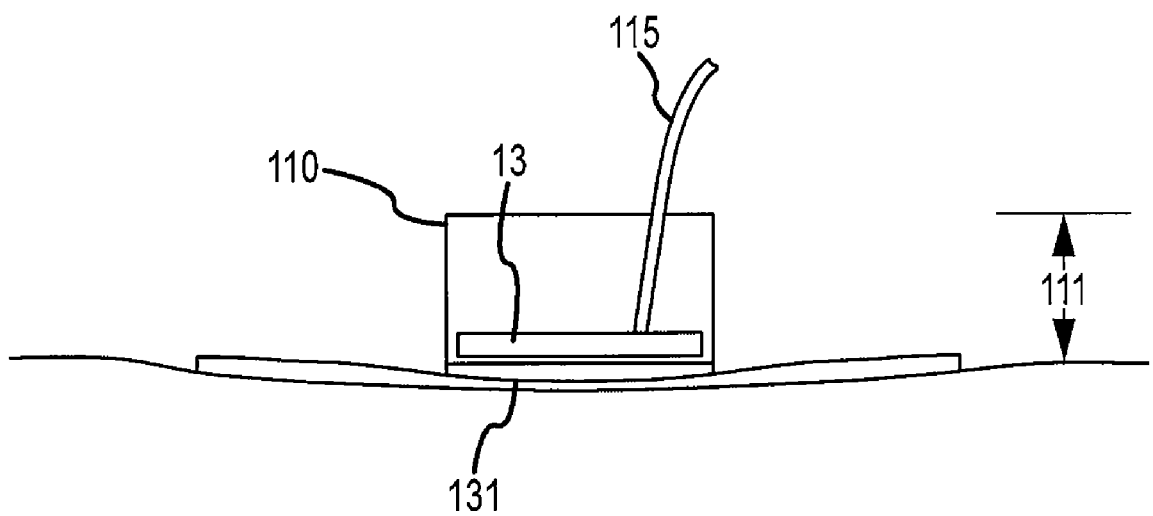
FIG. 2 is a schematic cross-sectional view of a probe according to certain embodiments.

Referring to FIG. 2, in a preferred embodiment, the four external cardiac probes 110A-D are ultrasonic transducers. The probes 1110A-D can have a relatively low profile with a height 111 of between approximately 1 cm to approximately 10 cm. Preferably, the height 111 is between approximately 2 cm to approximately 8 cm. The probes 110A-D can have a surface contact area of approximately 1 cm to 3 cm by approximately 3 cm to 8 cm, or approximately 3 to 24 cm$^2$. Preferably, the contact area is approximately 2 cm by approximately 5 cm, or approximately 10 cm$^2$.

In a preferred embodiment, the internal cardiac probe 110E is also an ultrasonic transducer. The probe 110E can be approximately 1 cm to 2 cm by approximately 2.5 cm to 3.5 cm, or approximately 2.5 to 7 cm$^2$. Preferably, the internal cardiac probe 110E is approximately 1.5 cm by 3 cm, or approximately 4.5 cm$^2$.

In a preferred embodiment, the external non-cardiac probe 110F can also be an ultrasonic transducer with a higher frequency than the cardiac probes 110A-E and thus adapted for imaging more superficial structures. For example, the external non-cardiac probe 110F may be used to identify superficial vascular structures outside the chest. As used herein, superficial can be understood to mean less than approximately 12 cm under the skin or preferably less than 10 cm under the skin. The probe 110F can be used when inserting a central line or a peripheral venous or arterial catheter. Alternatively or additionally, the probe 110F can be used for identifying large nerve bundles of the neck or an upper or lower extremity when performing a peripheral nerve blockade for surgical or post-operative pain control. The external non-cardiac probe 110F can have a height of between approximately 1 cm to approximately 12 cm. Preferably, the height is between approximately 2 cm and 8 cm. The external non-cardiac probe 110F can have a surface contact area of approximately 1 to 3 cm by approximately 8 to 10 cm, or approximately 8 to 30 cm$^2$. Preferably, the external non-cardiac probe 110F has a contact area of 2 cm by 8 to 10 cm, or 16 to 20 cm$^2$.

In a preferred embodiment, each of the external or internal probes 110 can be adapted for obtaining information suitable for two-dimensional imaging, three-dimensional imaging, B-mode, M-mode, color Doppler, and spectral Doppler output. The probes 110 can be built with piezo-electric crystals 113 adapted to emit ultrasonic signals. The probes 110 can include a suitable crystal array. For example, the cardiac probes 110 can be constructed with a phased array of crystals or a matrix of a phased array of crystals. The phased array of crystals may provide for a two dimensional pie-shaped cross-sectional image. The matrix may provide for a three dimensional image. The probes 110 adapted to image more superficial elements can be constructed with a linear array of crystals allowing for higher frequency imaging and may provide for a rectangular image. Other arrangements of crystals such as, for example, a circular array can be used and are within the scope of the disclosure. Moreover, mechanical transducers could be used in lieu of or in addition to the piezo-electric crystal type transducers described. In other embodiments the probes 110 can be adapted to obtain other information such as temperature, pressure, moisture, EKG signals, electrical signals, or other information indicative of patient condition. Accordingly, the probes 110 can take the form of a thermometer or a pressure transducer or sensor. The probes 110 can monitor other conditions and can take the form of other suitable devices adapted to detect and/or measure a condition.

Figure 3:
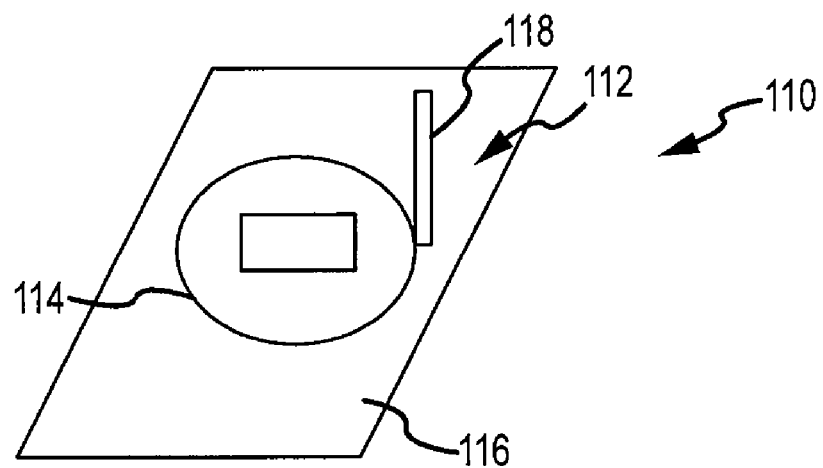
FIG. 3 is a schematic view of an external imaging plane mechanism.
Figure 4:
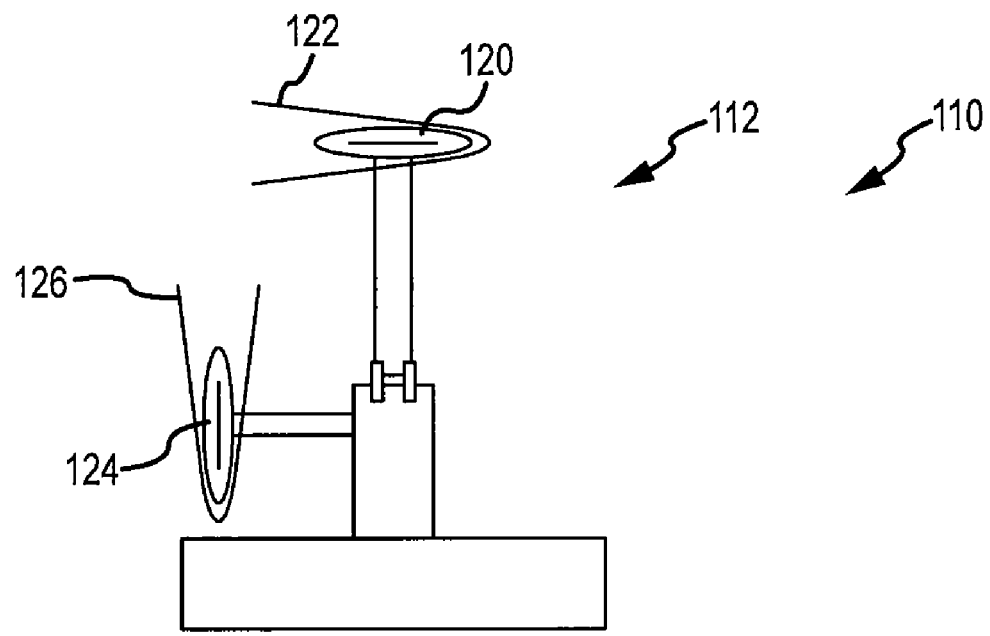
FIG. 4 is a schematic view of an internal imaging plane mechanism.
Figure 5:
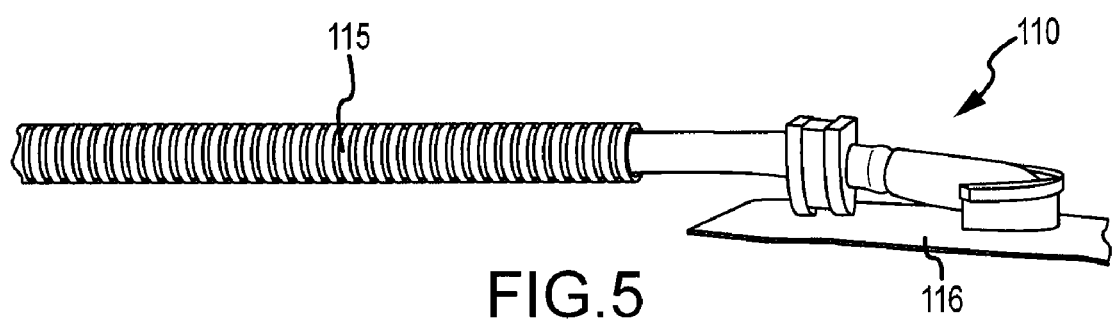
FIG. 5 is a side view of a probe according to certain embodiments.
Figure 6:
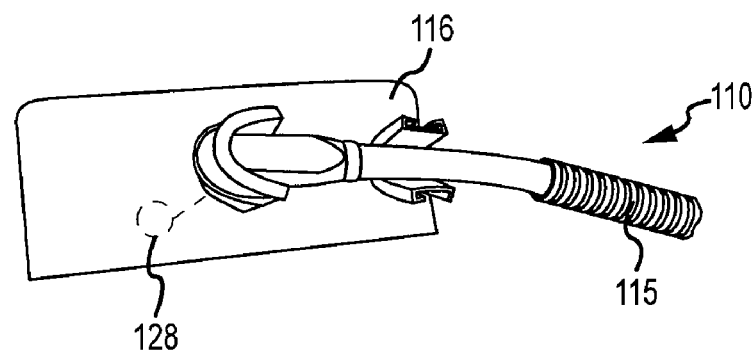
FIG. 6 is a top view of a probe positioned on a patient according to certain embodiments.
Figure 7:
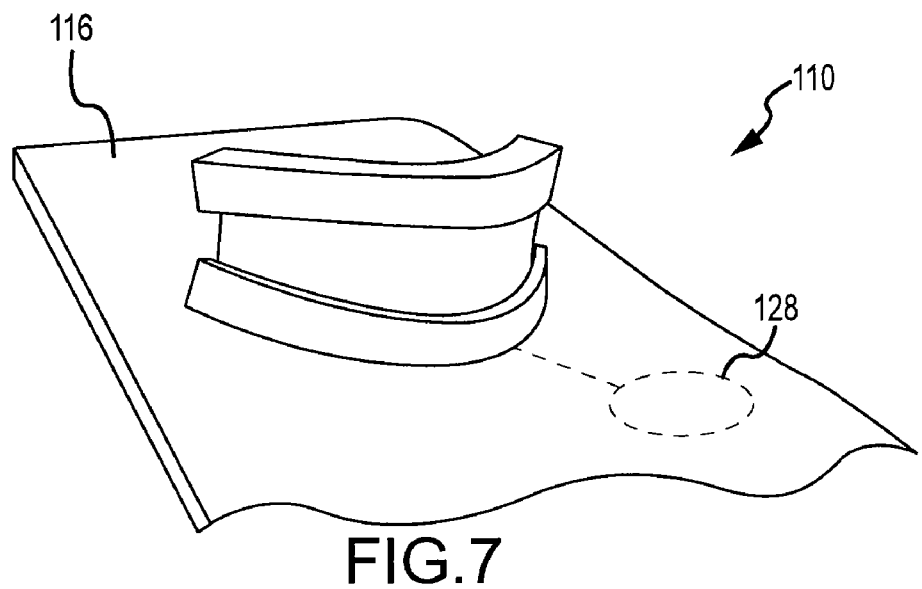
FIG. 7 is a front view of a connecting pad according to certain embodiments.

Referring generally to FIGS. 3 and 4, the probes 110 can include a variable probe view. In a preferred embodiment, the probe view can be adjusted with an imaging plane mechanism 112 allowing each probe 110 of the system to acquire optimal quality images with minimal or no intervention by the provider. The mechanism 112 can be adapted to allow for adjustment of the imaging plane of the probe 110 by providing a rotation angle adjustment and an elevation angle adjustment. In some embodiments, this mechanism 112 may be external and thus the imaging plane may be manually adjustable through physical adjustment of knobs, pins, levers, or other mechanical adjustment features. In other embodiments, the mechanism 112 may be internal and the imaging plane may be adjustable automatically by the controller 102 or manually through provider interaction with the controller 102.

In another embodiment, the patient interface 100 can include a housing 114 enclosing the probe 110 and the probe 110 can be adjustable within the housing 114. In this embodiment, the variable imaging plane mechanism 112 results from the interaction of the probe 110 with the housing 114. For example, the probe 110 can be rotatably positioned within the housing 114 about an axis substantially orthogonal to the patient body surface. The housing 114 may include an upper half and a lower half slidably connected about a circular perimeter allowing the upper half to rotate relative to the lower half. The probe 110 may be connected to the upper half allowing for the rotation of the probe 110 via rotation of the upper half relative to the lower half. The probe 110 can alternatively or additionally be pivotal about an axis substantially parallel to the patient body surface. The probe 110 may be positioned on a pivot rod extending from the housing 114 where the pivot rod is pivotally connected to the housing 114. The pivot rod may include a pivot knob for adjusting the pivotal position of the pivot rod thereby adjusting the pivotal position of the probe 110. In other embodiments, the probe 110 can be slidably positioned within the housing 114 allowing the probe 110 to translate in one or more directions parallel to the patient body surface. The probe 110 can be adapted to move in a direction relative to the housing 114 allowing for adjustability of the signal being emitted and/or received from the probe 110.

As shown in FIG. 3, an exemplary external imaging plane mechanism 112 is shown. As shown, the probe 110 may include a connecting pad 116, a housing 114 allowing for rotation of the transducer in a plane substantially parallel to the patient surface, and a lateral side bar 118 for pivoting the transducer in elevation. The external imaging mechanism 112 may be adjusted automatically with a series of controlled actuators and/or the system may be adjusted manually. In FIG. 4, an exemplary internal imaging plane mechanism 112 is shown. The mechanism 112 includes a rotation pulley 120 and cable 122 for rotating the transducer in a plane substantially parallel to the patient surface and a elevation pulley 124 and cable 126 for pivoting the transducer relative to the patient surface. As with the external mechanism 112, the internal mechanism 112 may be adjusted automatically and/or manually.

Referring to FIGS. 5-8, the probes 110 of the patient interface 100 can be positioned on a patient and connected to the patient with a securing system. The securing system can include a connecting pad 116 and the probe 110 can be affixed to the connecting pad 116. Alternatively, the connecting pad 116 can be omitted and the probe 110 can be adhered or externally secured directly to the body surface. Additionally, the securing system can include a probe detection device 128 adapted to trigger activation and calibration of an attached probe 110. As shown, the probe 110 can be connected to the controller 102 with a lead 115.

Figure 8:
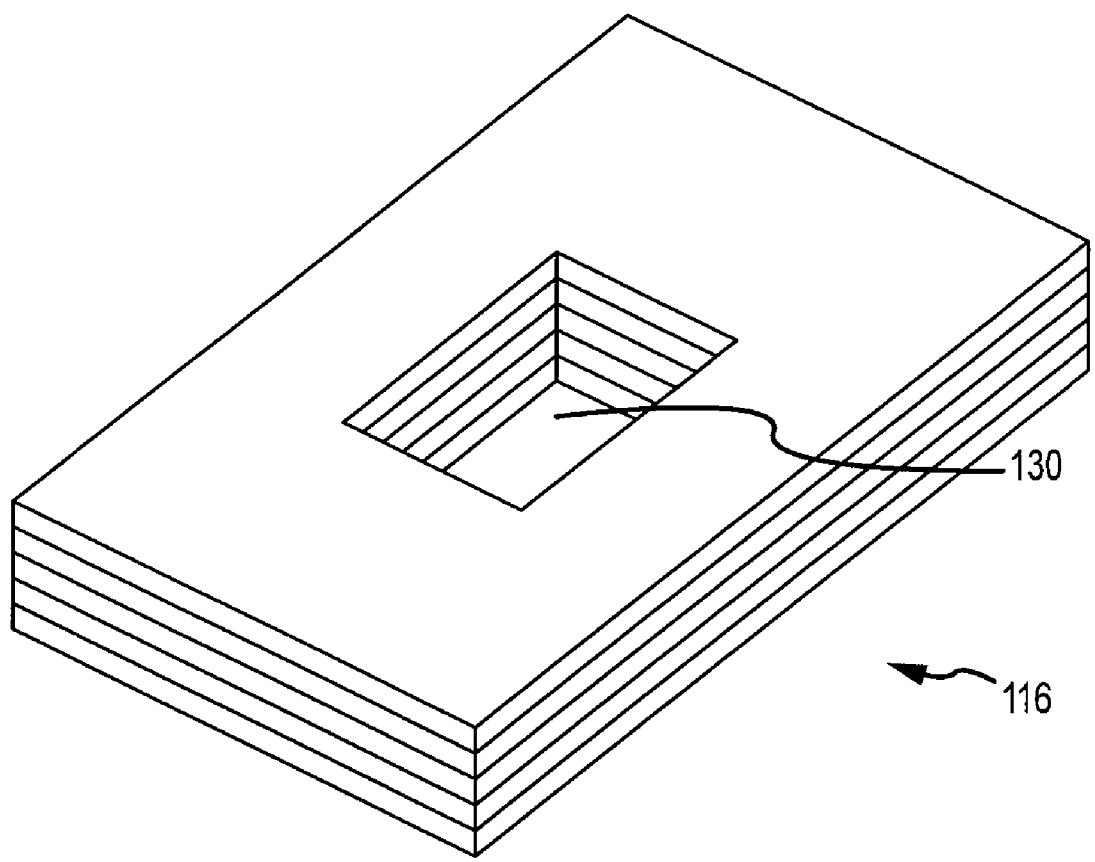
FIG. 8 is an isometric view of one embodiment of a connecting pad.

Referring particularly to FIG. 8, the connecting pad 116 can be an elastomeric material such as rubber or foam rubber. Preferably, the connecting pad 116 can be a latex free elastomeric material. The connecting pad 116 can include a single layer or multiple layers. The connecting pad 116 can include an aperture 130 for receiving a distal end of the probe 110. The aperture 130 can extend fully through the connecting pad 116 or can extend partially through the pad 116 as shown. Where the aperture 130 extends fully through the connecting pad 116, a distal end of the probe 110 can be placed in direct contact with the patient body surface through the aperture 130. Preferably, the contact between the probe 110 and the body surface is free of air voids. In some embodiments, an ultrasonic gel 131 can be provided between the probe 110 and the patient body surface as shown in FIG. 2. Where the aperture 130 extends partially through the connecting pad 116, the portion of the pad 116 between the probe 110 and the body surface can be solid or a liquid ultrasonic gel type material. Preferably, the portion of the pad 116 between the probe 110 and the body surface is free of voids or air pockets.

The probe detection device 128 can be integrated into the connecting pad 116. The device 128 may be adapted to sense that a probe 110 is connected to the pad 116 and may further be adapted to trigger activation and calibration of the probe 110. The probe detection device 128 can be in electrical and/or data communication with the controller 102 and can thus signal the controller 102 when a probe 110 is present. This communication may be facilitated through contact with the probe 110. That is, the device 128 may not be in communication with the controller 102 unless or until the probe 110 is attached to the connecting pad. Alternatively or additionally, the device 128 may be in direct communication with the controller 102 via a wired or wireless connection. In a preferred embodiment, the probe detection device 128 can be an electronic chip embedded in the connecting pad 116. The chip can include a contact or other sensing mechanism, such as a pressure sensor, for sensing the attachment of a probe 110 to the connecting pad 116. Upon attachment of a probe 110, the chip may be configured to signal the controller 102 to activate and calibrate the attached probe 110. In some embodiments, the connecting pads 116 may be adapted for use at a particular position or window. In these embodiments, the chip of the probe detection device 128 may be designed, configured, or otherwise adapted to indicate its position to the controller 102 such that the attached probe 110 can be activated and calibrated for a particular position on the patient.

The connecting pad 116 can be secured to the patient with a securing system. Preferably, the securing system is an adhesive and more preferably is a biocompatible adhesive. Alternatively or additionally, the connecting pad 116 can be connected to the patient with an external system in the form of a superimposed layer of adhesive material. For example an oversized piece of tape can be positioned over the probe 110 and the connecting pad 116 to secure the assembly to the patient. The superimposed adhesive material could alternatively include a central aperture for receiving the probe 110 so as to secure the connecting pad 116 to the body surface without covering the probe 110. The superimposed adhesive material can include a slit or slot through the portion of the material around the aperture to allow the material to be positioned around the lead 115 extending from the probe 110 and allowing the material to be easily removed and replaced. In yet another alternative, the external system can be one or more bands, belts, or straps positioned to secure the probe 110 and/or connecting pad 116 to the patient's body surface. The external system can extend around the patient's body and be drawn tight or connect to a supporting table in the form of a tie-down. The external system can extend across the surface of the probe 110 and/or connecting pad 116 or it can be secured to the probe 110 and/or connecting pad 116 via a hook, a loop, a button, a hook and loop system, or some other securing mechanism. The external system can connect to itself with any or a combination of any of the above listed connections.

The patient interface 100 can be in data communication with the controller 102 via a lead 115, in the case of a wired connection, or the patient interface 100 can be in wireless data communication with the controller 102. Where a wired connection is provided, the connection can include power flowing to the patient interface 100 from the controller 102 or the patient interface 100 can includes its own power source. Where wireless communication is provided, the patient interface 100 can include its own power source. The power source, in either a wired or wireless condition, can include probe specific batteries, or an overall patient interface battery connected to all of the probes 110.

The probe or probes 110 can be the same or similar to the probe described in U.S. Provisional Patent Application No. 61/140,767 filed on Dec. 24, 2008 entitled Peripheral Ultrasound system (apparatus and method) for automated and uninterrupted data acquisition. The probe or probes 110 can alternatively be the same or similar to the device described in U.S. Pat. No. 5,598,845 to Chandraratna et al. The probe or probes 110 can alternatively be the same or similar to the device described in U.S. Pat. No. 6,261,231 to Damphousse. The probe or probes 110 may alternatively include features and combinations of any or all of the above disclosures.

Figure 9:
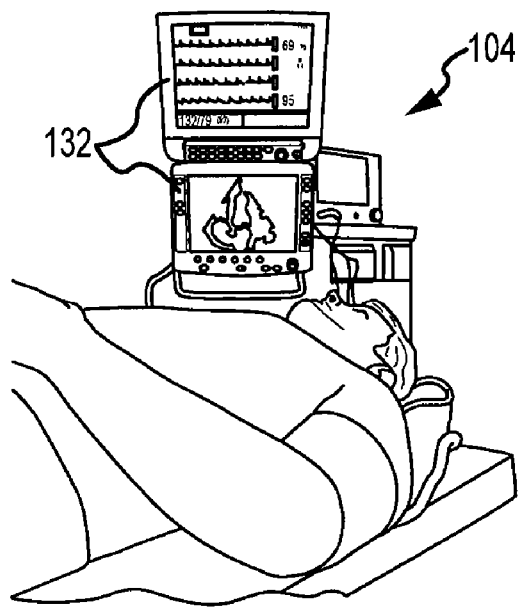
FIGS. 9 & 10 are each front views of a display according to certain embodiments.
Figure 10:
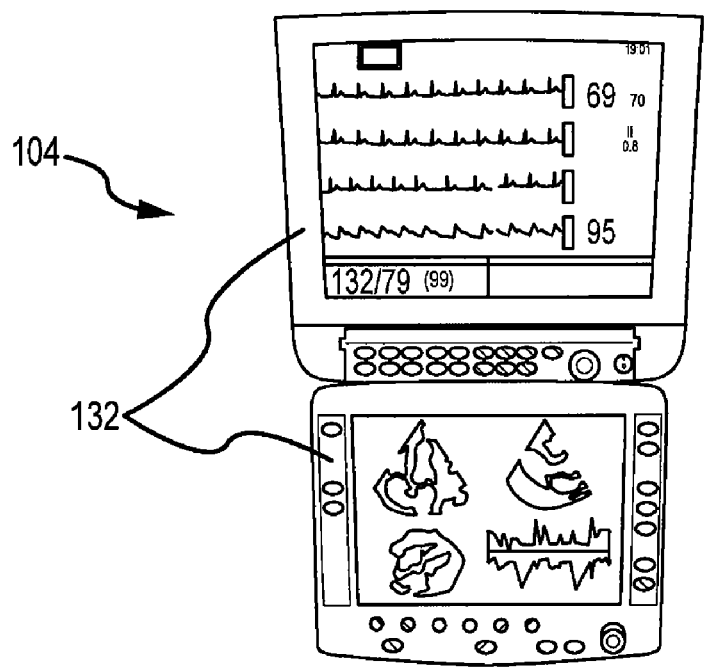

Referring now to FIGS. 9-10, a provider interface 104 is shown. The provider interface 104 can include one or more provider output devices and one or more provider input devices. Regarding the provider output devices, a display 132 in the form of a cathode-ray tube (CRT), liquid crystal display (LCD), Plasma based display, or another type of display 132 can be provided. The provider output device can also include a printer and can include a speaker for transmitting sound type output in the form of tones or verbal output.

In a preferred embodiment, the display 132 may be large enough to present clear ultrasound images and image acquisition sequencing. For example, the display 132 may be adapted to present four digital loops at the same time as shown in FIG. 10. More or fewer loops can also be provided.

The display 132 may also be adapted for displaying an EKG signal or a blood pressure value. In one embodiment, the display 132 can show a value for continuous left-sided cardiac output. For example, the display 132 may read 5 Liters/min. Additionally, consideration can be given to the workspace of the provider and as such, the display 132 can be similar in size to a monitor display on an EKG or a blood pressure monitor. Other output type devices may be provided.

Regarding the input devices, a keyboard, mouse, or joystick can be provided. Additionally, a touchpad can be included or a microphone for receiving an audio type input can be provided. In a preferred embodiment, the display 132 output device can double as an input device via a touch screen for receiving input information from the provider. Alternatively or additionally, the display 132 may include buttons or switches as shown in FIGS. 9 and 10. Other input devices can also be used.

Figure 11:
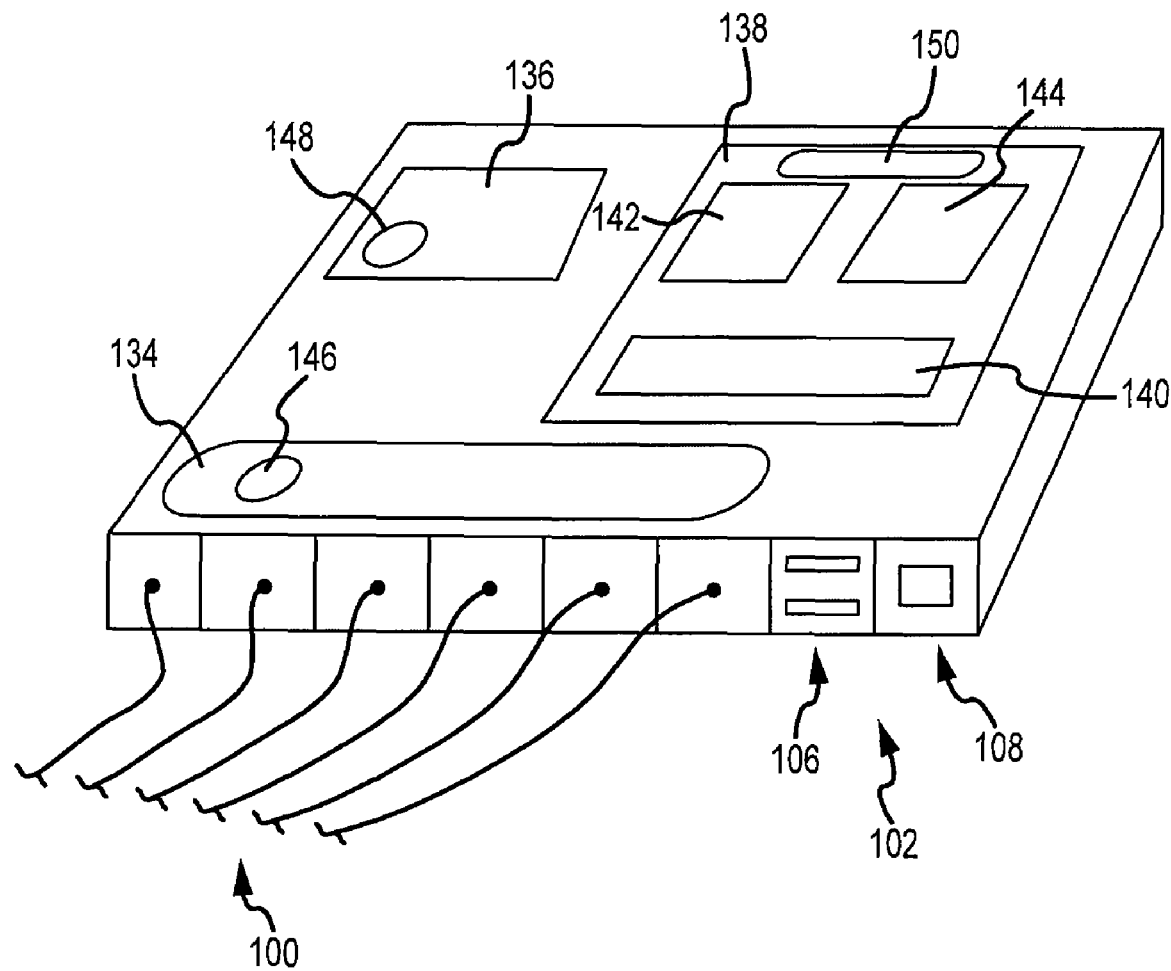
FIG. 11 is a schematic view of a controller according to certain embodiments.

Referring to FIG. 11, the auxiliary device interface 106 can include one or more ports on the controller 102 for connection of the auxiliary devices. The ports can be any suitable plug-type socket on the controller 102 for receiving a lead from an auxiliary device. Alternatively, the auxiliary device interface 106 can be a wireless based interface for receiving input information from an auxiliary device.

Still referring to FIG. 11, the network interface 108 can include one or more jacks on the controller 102 for connection to a network. This jack can be any suitable connection socket on the controller 102 for receiving a network cable for connection to a near by network jack. For example, an Ethernet connection jack, USB port, or phone jack may be provided. Other suitable connection systems can be provided. The network interface 108 can also include a wireless based interface for communicating with a wireless network.

Referring still to FIG. 11, a controller 102 is shown. The controller 102 can include a computer adapted to connect and control several interfaces. Alternatively, the controller 102 can be more particularly constructed for a particular process or purpose. The controller 102 can be in the form of a field programmable gate array, a mixed signal micro controller 102, an integrated circuit, a printed circuit board, or the controller 102 can be created in a virtual product development platform such as LabVIEW or the like. Accordingly, the controller 102 can include any combination of hardware and software and can be adapted for a particular purpose.

Processes and analyses performed by the controller 102 can be performed by modules including hardware, software, or some combination of hardware and software. In a preferred embodiment, the controller 102 includes a patient interface module 134, an analysis module 136, and a provider interface module 138. The provider interface module 138 may further include a clinical management module 140, an electronic reporting module 142, and a Diagnosis Related Group (DRG) reporting module 144. Other modules can be included and can be adapted for receiving, sending, interpreting, or analyzing data and any combination of processes can also be included in any given module.

The controller 102 can include hardware and/or software to interact with and control any or all of the several included modules and/or interfaces. Moreover, any combination of the software, hardware, and/or modules is within the scope of the present disclosure. Accordingly, complete or partial overlap of the functionality of the modules should be understood to exist in certain circumstances.

The controller 102 can include a patient interface module 134 adapted to control the patient interface 100. More particularly, the patient interface module 134 can be adapted to drive the probes 110. In a preferred embodiment, the patient interface module 134 may include an image generating module 146. The image generating module 146 can be adapted to control ultrasonic transducers and can be adapted to generate, transmit, and receive ultrasonic waves via the transducers. Accordingly, the image generating module 146 can perform beamforming, array beamforming, and all signal processing functions. The image generating module 146 can produce two-dimensional and three-dimensional imaging as well as B-mode, M-mode, color Doppler, and spectral Doppler data points. In the case of alternative or additional types of probes 110, the patient interface 100 can be adapted to initiate suitable probe signals and/or receive probe data.

In addition, the patient interface module 134 can control the adjustment of the probe view. That is, where the probe 110 is adjustable relative to its position on the patient, the patient interface module 134 can control actuation devices for rotating, pivoting, translating, or otherwise adjusting the position and probe view obtained by the probe 110. Alternatively or additionally, the adjustment of the probes 110 may be manually performed with knobs or other physical adjustment devices.

The patient interface module 134 can be adapted to periodically or continuously collect data via the probes 110 of the patient interface 100. In a preferred embodiment, the patient interface module 134 can automatically acquire ultrasound-generated data points at a selected time interval. For example, the patient interface module 134 can be set by the provider to obtain cardiovascular information about a patient every minute, every two minutes, every 10 minutes, or at any time interval selected by a provider.

Figure 12:
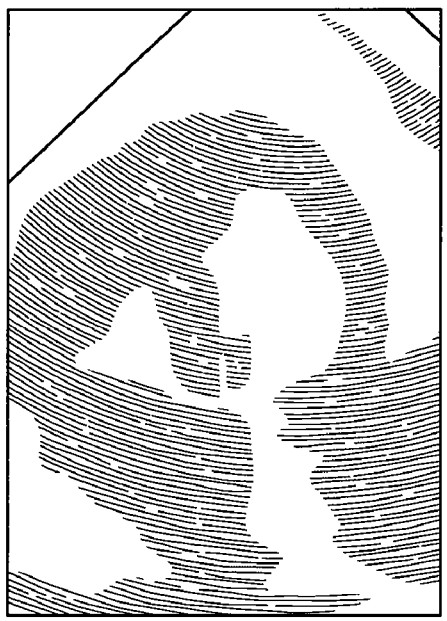
FIG. 12 is an exemplary 2D black and white ultrasound image display according to certain embodiments.
Figure 13:
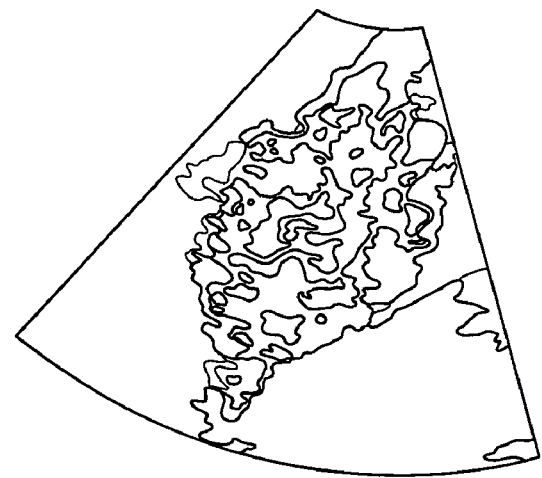
FIG. 13 is an exemplary color Doppler image display according to certain embodiments.
Figure 14:
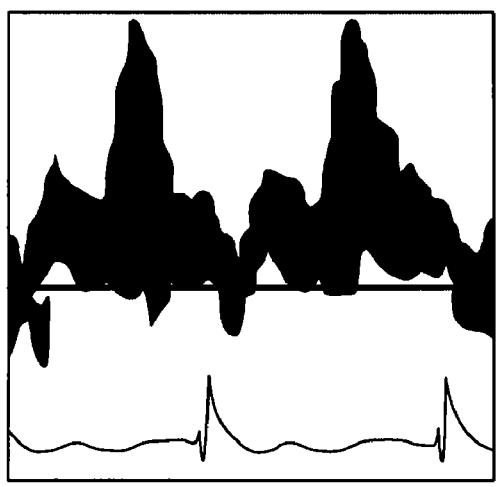
FIG. 14 is an exemplary spectral Doppler image display according to certain embodiment.

The patient interface module 134 can also be adapted to control the manner in which the probes 110 collect the data. That is, the patient interface module 134 can select from one or more modes for any given probe 110 to use when collecting information. For example, a first mode of data collection may include a two-dimensional (2D) black and white image of the moving heart muscle and valves, as shown in FIG. 12. In this mode, one or more heart beat cycles may be acquired for each 2D image cross-section. The heart beat cycles can be shown on the display 132 in a video loop format called a 2D clip such that the heart looks to be beating continuously. A second mode of data collection may include color Doppler imaging. This mode may also include a region of interest (ROI) box superimposed on a 2D ultrasound image. The ROI box may be defined by the provider by clicking and dragging a mouse to form a box. Other known methods of selecting a box may be used and other shapes other than a box may also be used. Within the ROI, the velocity and direction of the blood flow during a cardiac cycle may be shown using a range of shades of blue and red colors. The blue and red colors may reflect the direction of flow toward or away from the probe 110. (i.e., red being toward the probe 110 and blue being away from the probe 110.) In FIG. 13, the blood flow is toward the probe and would appear on a color display in red. Similar to the first mode, this mode may also be shown on the display 132 in a video loop format. A third mode of data collection may include spectral Doppler tracings. Similar to the second mode, this third mode may also use a ROI defined by the provider. The spectral Doppler may measure and display the direction and velocity of the blood flow within the ROI as shown in FIG. 14. The spectral Doppler mode allows calculation of clinically useful volumes, flows, and pressures using the measured velocities.

After imaging and acquisition, all ultrasound-generated data may be recorded and stored in a memory of the controller 102. Alternatively or additionally, the data may be directly communicated to the analysis module 136 for further processing. The memory of the controller 102 may be a digital memory of a hard drive where a computer system is provided as the controller 102. Other memory types can be used. The ultrasound-generated information can allow for determination of the assessment of ventricular contractility, valvular structure and function, cardiac output and filling pressures.

The controller 102 can also include an analysis module 136. The analysis module 136 can be adapted for use with a specific type of probe 110 or it may be a more general module adaptable for use with several, and/or differing types, of probes 110. The analysis module 136 can use information received from the probes 110 and can process that information into additional data or results.

In a preferred embodiment, the analysis module 136 can be adapted for use with ultrasonic transducer type probes 110. The analysis module 136 can include one or more algorithms configured for analyzing the circulatory function information obtained by the transducers and for developing cardiovascular determinants. These algorithms may include interpretive processes or more calculated processes depending on the information received and the determinants being developed. As discussed above, the information received may be provided in one of at least three forms including: a) 2D or 3D black and white images b) Color Doppler images, and c) Spectral Doppler tracings. The determinants being developed and used for monitoring patients can include: contractile function, valvular function, cardiac output, and filling pressures.

These determinants can be developed by the analysis module 136 through interpretation of one or more types of ultrasound-generated images and/or calculations based on ultrasound data. In some cases, for example the cardiac output, the development of the determinant may be a substantially calculated process. However, in other cases, for example the contractile function, the development of these determinants may be a substantially interpretive process. For example, determining whether the contractile function is normal requires knowledge of how a normal contracting heart appears. Accordingly, this interpretive process may include comparing a captured image clip to image clips with known values or categorizations. Image recognition software may be employed for comparing the captured clip to a series of stored clips. A correlation algorithm for making the comparison may be based on previously defined visual assessment pattern correlations, where the visual assessment was performed by clinical diagnostic experts in cardiac ultrasound imaging and the clinically adequate and relevant correlation is made possible by evaluating and computing a large number of cases and images. Alternatively or additionally, where the provider is viewing the display 132, the provider may interpret the image or may compare the image to the database of images. Accordingly, the provider may develop the determinants separate from and/or in addition to the system.

In one embodiment, the correlation algorithm may include analyzing a captured image clip with an image recognition module 148 and may further include comparing the result to a series of stored image clips in a database. Each of the stored image clips in the database may be assigned to a category based on previous clinical studies as discussed above. A rating may be given to the comparison of the captured image clip to a respective stored image clip for each comparison made. The captured clip may be compared to all of the stored clips and a category may be assigned to the captured image clip consistent with those image clips to which the comparison had the highest ratings. Alternatively or additionally, a trend of a likeness to a given category of stored clips may be recognized and a category may be assigned accordingly. In either case, the captured image clip may be categorized consistent with the stored image clip or clips that it most closely resembles. Other algorithms may be followed to correlate a captured image clip with a category of clips in a database and these other algorithms are within the scope of the present disclosure.

Regarding the contractile function, the analysis module 136 can develop both right and left contractile function information by analyzing a 2D and/or 3D captured image clip provided by the patient interface 100. The captured image clip can be compared to image clips in a contractile function image clip database and a category may be assigned to the captured image clip as shown in FIG. 15. Accordingly, the correlation algorithm may be used to categorize the acquired 2D image clip into a a) hyperdynamic, b) normal, c) moderately reduced, or d) severely reduced ventricular contractile function pattern.

Regarding the valvular function, the analysis module 136 can provide an assessment of the presence and severity of mitral, aortic, and tricuspid valve regurgitation by analyzing color Doppler images. A color Doppler image clip of these valves can be captured by the patient interface 100. The analysis module 136 can compare the image to image clips in respective mitral, aortic, and tricuspid image clip databases. A category can be assigned to the captured image clip for each valve. Accordingly, the correlation algorithm can be used to categorize the valvular function of each valve as shown in FIG. 15. For the mitral valve, the algorithm may categorize the captured image clip into a a) mild, b) moderate, or c) severe mitral regurgitation pattern. For the aortic valve, the algorithm may categorize the captured image clip into a a) mild, b) moderate, or c) severe aortic regurgitation pattern. For the tricuspid valve, the algorithm may categorize the captured image clip into a a) mild, b) moderate, or c) severe tricuspid regurgitation pattern.

Regarding the cardiac output and filling pressures, the analysis module 136 can utilize spectral Doppler tracings to determine these and other related values. For example, spectral Doppler can be used by the analysis module 136 to provide a basic assessment of the left ventricular diastolic function, the left ventricular filling pressure, the systolic pulmonary artery pressure, the presence and severity of aortic stenosis, and the cardiac output.

Regarding diastolic function, a spectral Doppler tracing relating to the mitral inflow (i.e., the mitral inflow tracing) can be used to obtain an image clip with the patient interface 100. The captured clip can be compared to stored clips in a diastolic dysfunction image clip database and a category can be assigned to the captured image clip as shown in FIG. 15. Accordingly, the captured image clip can be categorized into a a) mild, b) moderate, or c) severe diastolic dysfunction pattern.

Regarding the left ventricular filling pressure, a general filling pressure determinant can be developed using a spectral Doppler tracing relating to the pulmonary venous flow. A captured image can be obtained of the spectral Doppler tracing using the patient interface 100, a comparison can be made to a database of filling pressure image clips, and a category can be assigned to the captured clip as shown in FIG. 15. Accordingly, the captured clip can be categorized into a a) normal or b) elevated left ventricle filling pressure pattern. Alternatively or additionally, the filling pressure can be estimated by calculating the ratio between two spectral Doppler direct measurements. The peak velocity of the E wave of the mitral inflow and of the e' mitral annulus wave of the tissue Doppler may be directly measured using spectral Doppler. The ratio of the E wave velocity to the e' mitral annulus wave velocity can provide a numerical estimate of the left ventricular filling pressure. Once calculated, the filling pressure can be numerically compared to known normal pressures. For example, approximately 5-15 mm Hg may be considered normal and values above or below this range may be deemed high or low respectively.

Regarding the systolic pulmonary artery pressure, a spectral Doppler tracing of the velocity of the red cells of the systolic tricuspid regurgitation jet may be obtained by the patient interface 100. A direct measurement of the peak velocity may provide a clinically relevant estimation of the systolic pulmonary artery pressure using the simplified Bernoulli equation. The normal range of the systolic pulmonary artery pressure may be less than 30 mm Hg.

Regarding mitral and aortic stenosis, direct measurements may be made of spectral Doppler tracings to develop these determinants. For mitral stenosis, the mean gradient of pressure may be directly measured from the spectral Doppler tracing of the mitral inflow and the severity of mitral stenosis may thus be defined as either a) mild (mean gradient of 5 mm Hg), b) moderate (>5 and <15 mm Hg), or c) severe (>15 mm Hg.) For aortic stenosis, the peak velocities may be directly measured from the spectral Doppler tracing of the red cells in the left ventricular outflow tract (LVOT) and at the aortic valve. The ratio of the peak velocities of the red cells in the LVOT to those at the aortic valve may define the severity of aortic stenosis as either a) mild if the ratio is 1:2, b) moderate if the ratio 1:3, or c) severe if the ratio is 1:4.

Regarding the cardiac output, two direct measurements may lead to the development of this determinant. The profile of the spectral Doppler tracing obtained from the LVOT during systole may be used to determine the average distance red cells travel during this event. That is, the area under the spectral Doppler tracing, or the integral of the tracing, may provide this average distance. Additionally, the diameter of the LVOT may be directly measured allowing for the geometric calculation of LVOT area. With those two data points, the average distance of red cell travel and LVOT area, the patient stroke volume and therefore the cardiac output can be calculated. A normal cardiac output may be from 5 to 6 L/min.

The controller 102 can also include a provider interface module 138 for receiving instructions from the provider and for displaying patient interface 100 or analysis data. The provider interface module 138 can include software and/or hardware suitable for receiving and interpreting information from several input devices such as a mouse, keyboard, touch screen, joystick, or other input devices. In the case of audio input, the provider interface may include a voice recognition software for interpreting provider commands. The provider interface module 138 can include a display module 150 including software and/or hardware for displaying graphs, images, text, charts, or other displays for review and/or interpretation by a provider or other user. Other software and/or hardware can be provided for other output types such as printing. In a preferred embodiment, the display module 150 can include software and/or hardware for a series of menus accessible by the provider for producing reports, medical record data, billing information, and other output types.

In a preferred embodiment, the display module 150 can be adapted for producing image displays adapted to display anatomy scanned by the probes 110. That is, the display module 150 can be adapted to show the data obtained from the several modes of operation of the probes 110. In a preferred embodiment, the probes 110 produce ultrasound data and the ultrasound-generated data may be displayed on the monitor as standard ultrasound images. As shown in FIGS. 10 and 12, the 2D cross-section images may be black and white moving clips of the heart beating. The images may be looped video clips giving the end-user the appearance of a continuous heart beating. As shown in FIG. 13, the color Doppler images may be 2D cross-section images with a ROI color box superimposed on a valvular structure and showing the direction and velocity of the blood flow based on the shade and color displayed. This image may also be a looped video clip showing the heart beating. As shown in FIG. 14, the spectral Doppler tracings may be still images displaying a graphical representation of the variation of the measured red cells velocities over time, usually one cardiac cycle. In another embodiment, the 2D images may be displayed as 3D images and provide the equivalent information on ventricular contractility and valvular structure and function.

The controller 102 can include a clinical management module 140. The clinical management module 140 can be adapted to receive data from the analysis module 136 and/or the provider interface module 138 and present suggested clinical strategies to the provider. The clinical management module 140 can be based upon knowledge and studies conducted regarding suitable clinical management of patients. For example, the clinical management module 140 can include suggested clinical strategies relating to a particular system of the human body, such as the nervous system, digestive system, or circulatory system. The clinical management module 140 can alternatively or additionally include suggested clinical strategies relating to particular organs or conditions. Strategies relating to other aspects of patients requiring clinical management can be included and the clinical management module 140 can be directed to one or more of these aspects of patient management. Accordingly, the clinical management module 140 can be adapted to provide a menu or other selection screen allowing for the focusing of the device for a particular clinical management.

In a preferred embodiment, the clinical management module 140 can be directed toward managing the anesthesia or hemodynamic status of a patient. Preferably, the clinical management module 140 can be adapted for use while the patient undergoes an anesthetic, perioperative, or critical care procedure. Accordingly, the clinical management module 140 can be adapted for use with the analysis module 136 and patient interface 100 described above. The clinical management module 140 can receive ultrasound or other data from the analysis module 136 and provide a suitable clinical management strategy. Alternatively or additionally, the data can be provided by the provider upon interpretation of the ultrasound generated images and/or data.

In the preferred embodiment, the clinical management module 140 may use the cardiac output and the left ventricular filling pressures as first order data points to manage a patient's hemodynamic status. Additionally, the clinical management module 140 may use the valvular function and the biventricular contractile function as second order data points to manage a patient's hemodynamic status. The clinical management module 140 can assess the primary and/or secondary order data points and suggest a suitable clinical strategy. The clinical strategy may suggest the adjustment of one or more cardiovascular determinants. In particular, the strategy may suggest the adjustment of cardiovascular control determinants such as the preload, the afterload, the heart rate, and the ventricular contractility. The clinical strategy can be followed by the provider or the provider may choose not to follow the strategy.

Figure 16:
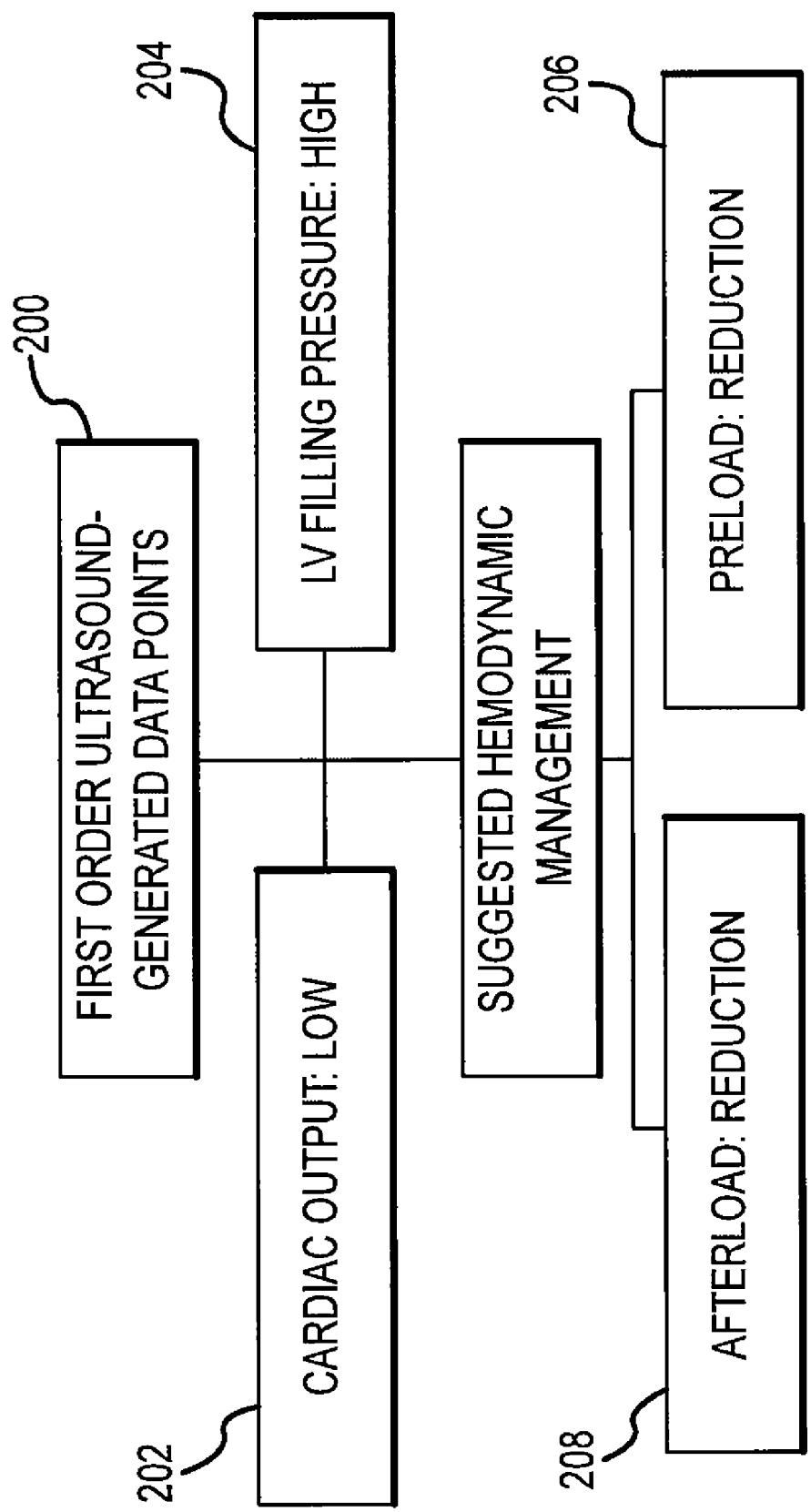
FIGS. 16-27 are each charts reflecting clinical management strategy processes according to one or more embodiments.
Figure 17:
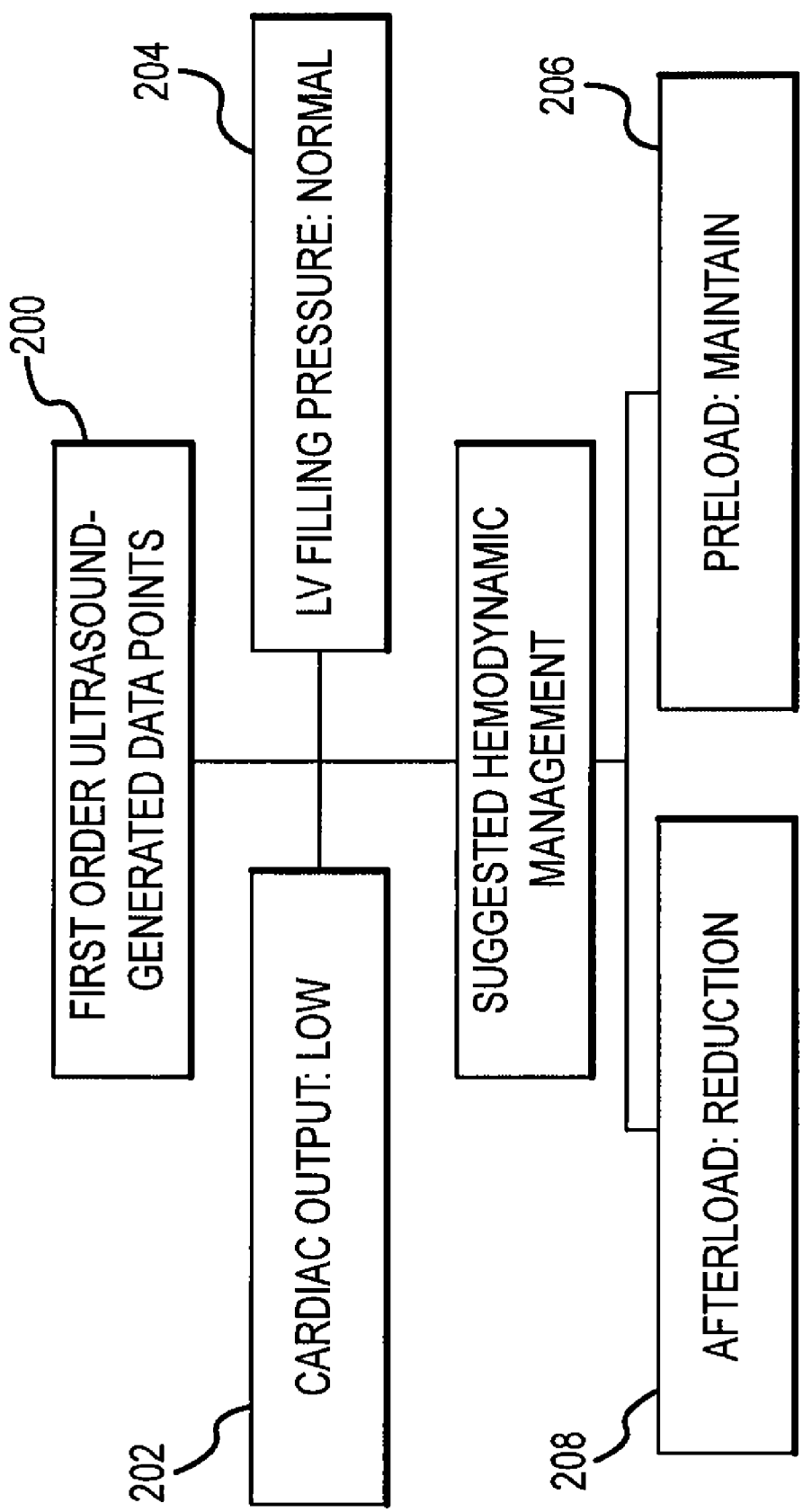
Figure 18:
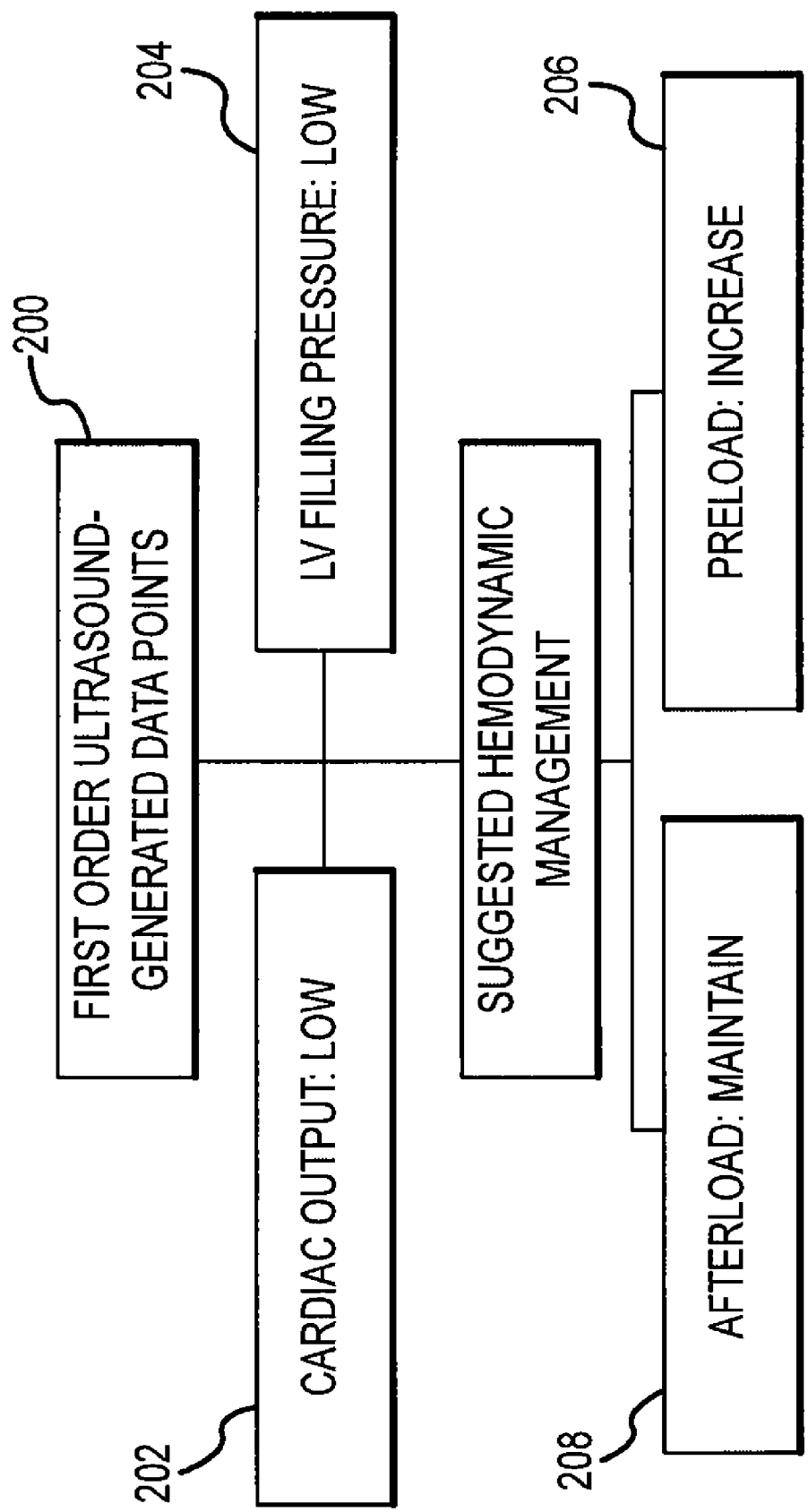
Figure 19:
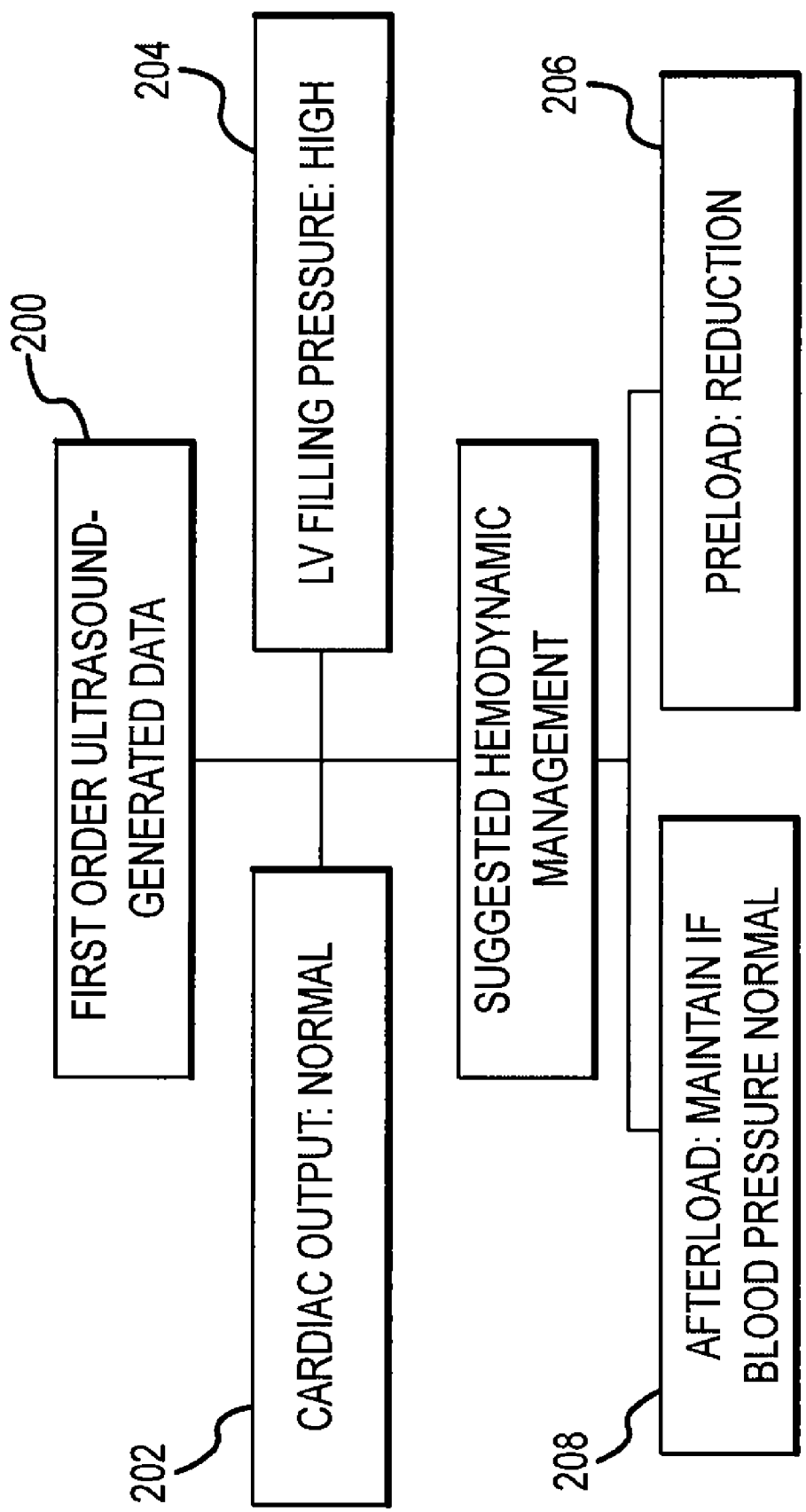
Figure 20:
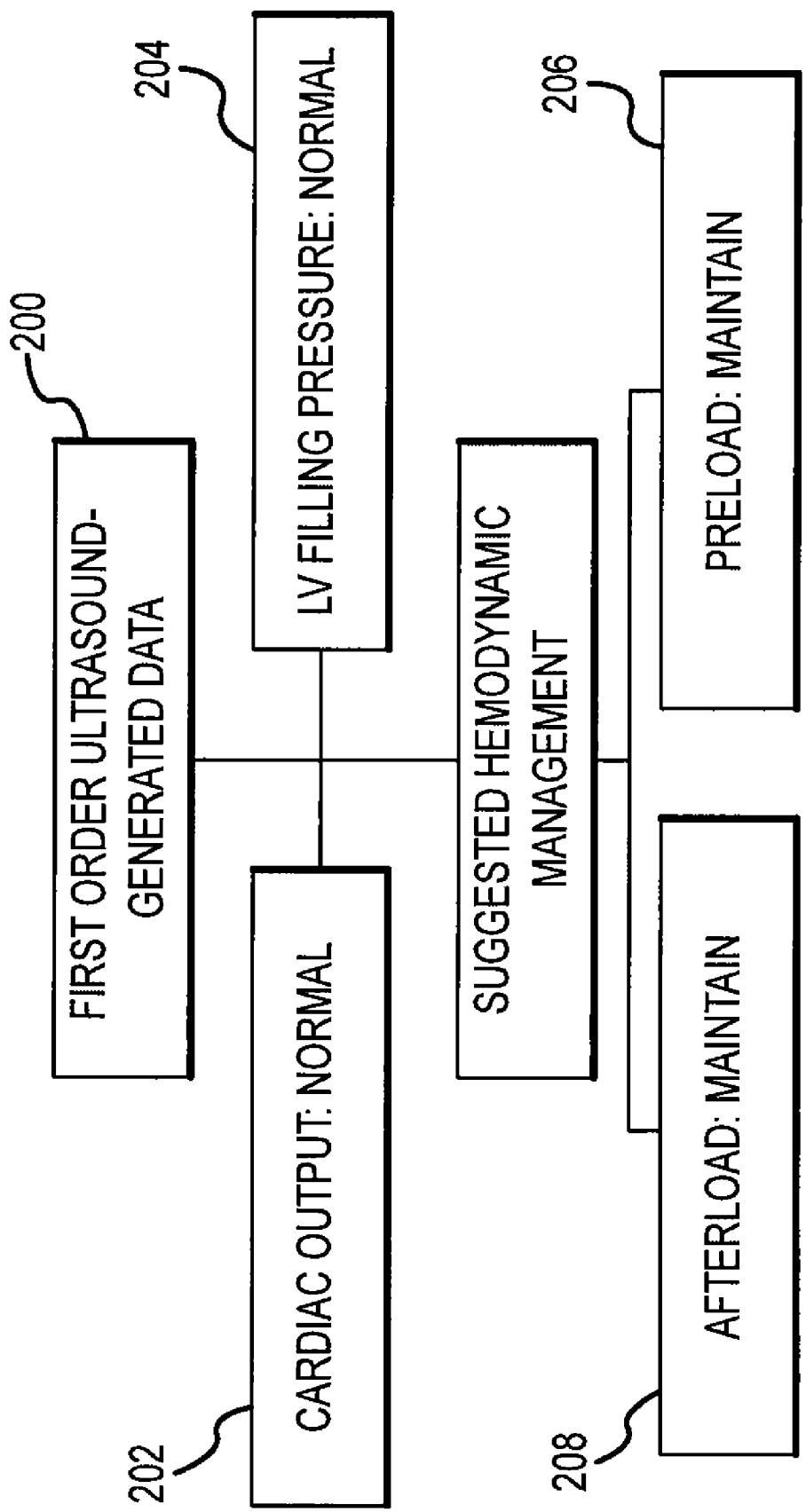
Figure 21:
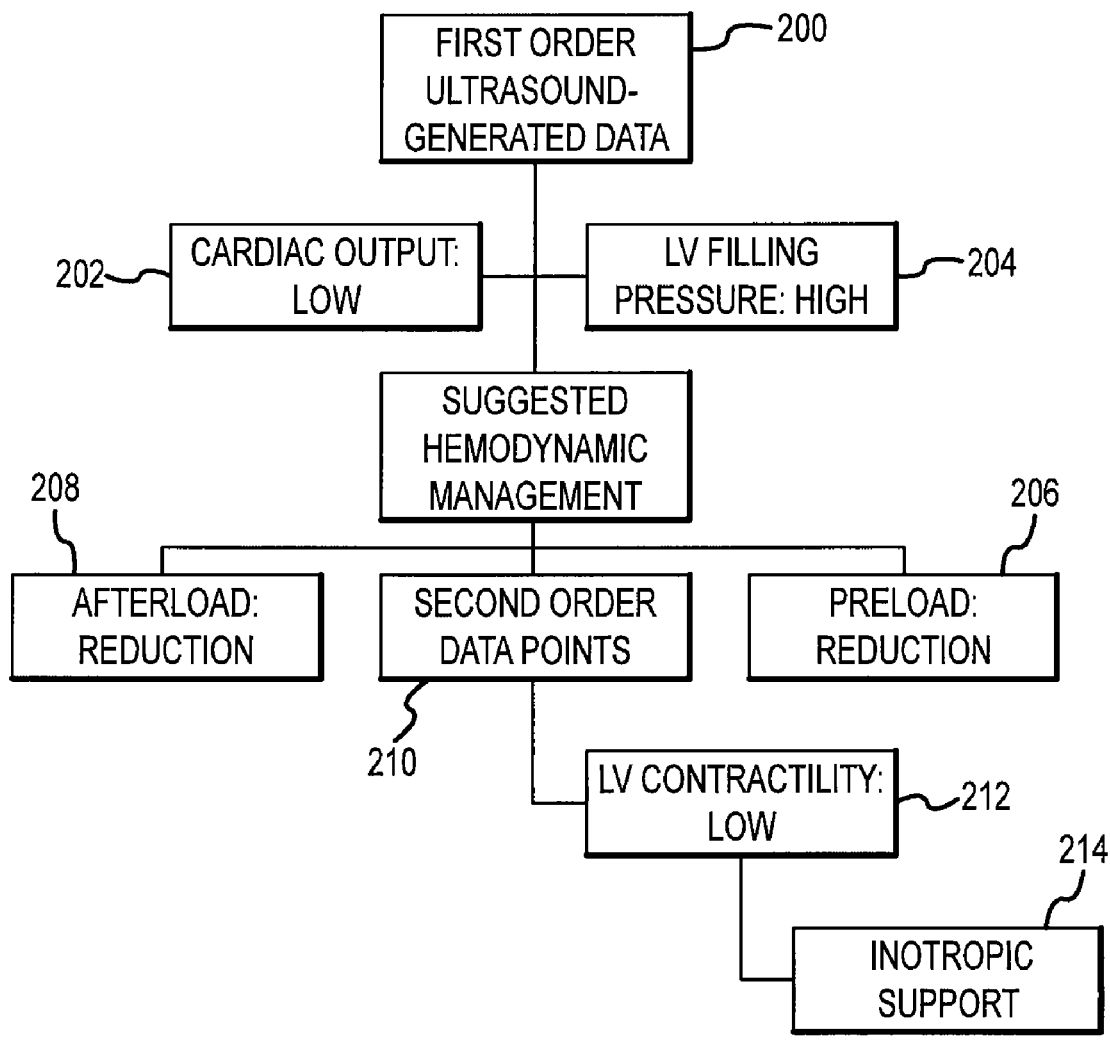

As shown in FIG. 16-25, the clinical management module 140 can include one or more algorithms to be followed based upon the input information provided. Referring to FIG. 16, in clinical cases where the first order data points 200 indicate a low cardiac output 202 and high filling pressure 204, the clinical management module 140 may suggest that the provider reduce the preload 206 and reduce the afterload 208 (Strategy 1). Referring to FIG. 17, where the first order data points 200 indicate a low cardiac output 202 and filling pressure 204 within normal limits, the module may suggest that the provider reduce the afterload 208 and maintain the current preload 206 (Strategy 2). In FIG. 18, the first order data points 200 indicate a low cardiac output 202 and low filling pressure 204 and the strategy suggests that the provider increase the preload 206 (Strategy 3). In FIG. 19, the first order data points 200 indicate a normal cardiac output 202 and high filling pressure 204 and the strategy suggests that the preload 206 be reduced and that the systemic blood pressure be maintained if within normal limits (Strategy 4). The strategy may also suggest that the afterload 208 be reduced if the systemic blood pressure is high (Strategy 4). Referring to FIG. 20, where the first order data points 200 indicate a normal cardiac output 202 and normal filling pressures 204, the strategy may be to maintain the current preload 206 and afterload 208 conditions (Strategy 5). As shown in FIG. 21, in clinical cases where the cardiac output 202 remains low despite optimal preload 206 and afterload 208 management and the second order ultrasound-generated data points 210 indicate a reduced contractile function 212, the strategy may be made to use inotropic support 214 (Strategy 6).

Figure 22:
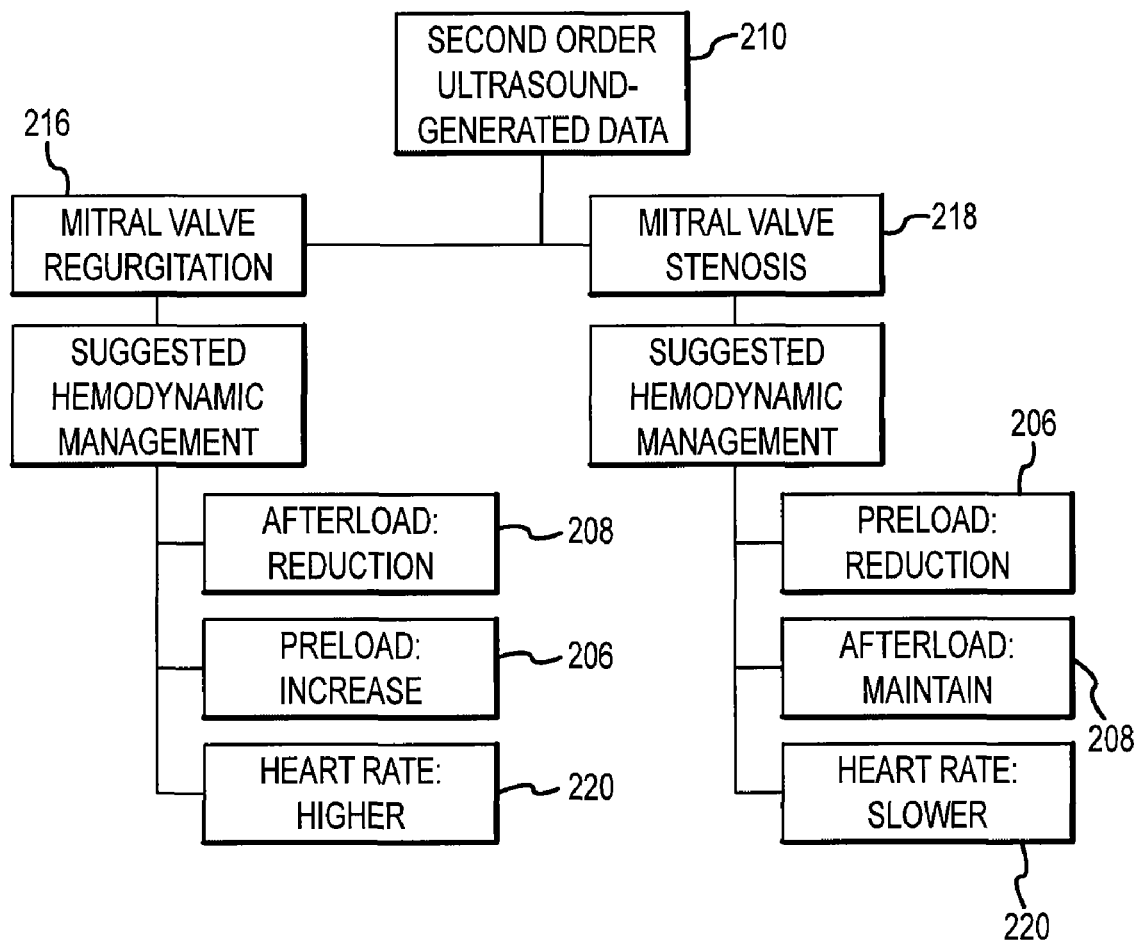
Figure 23:
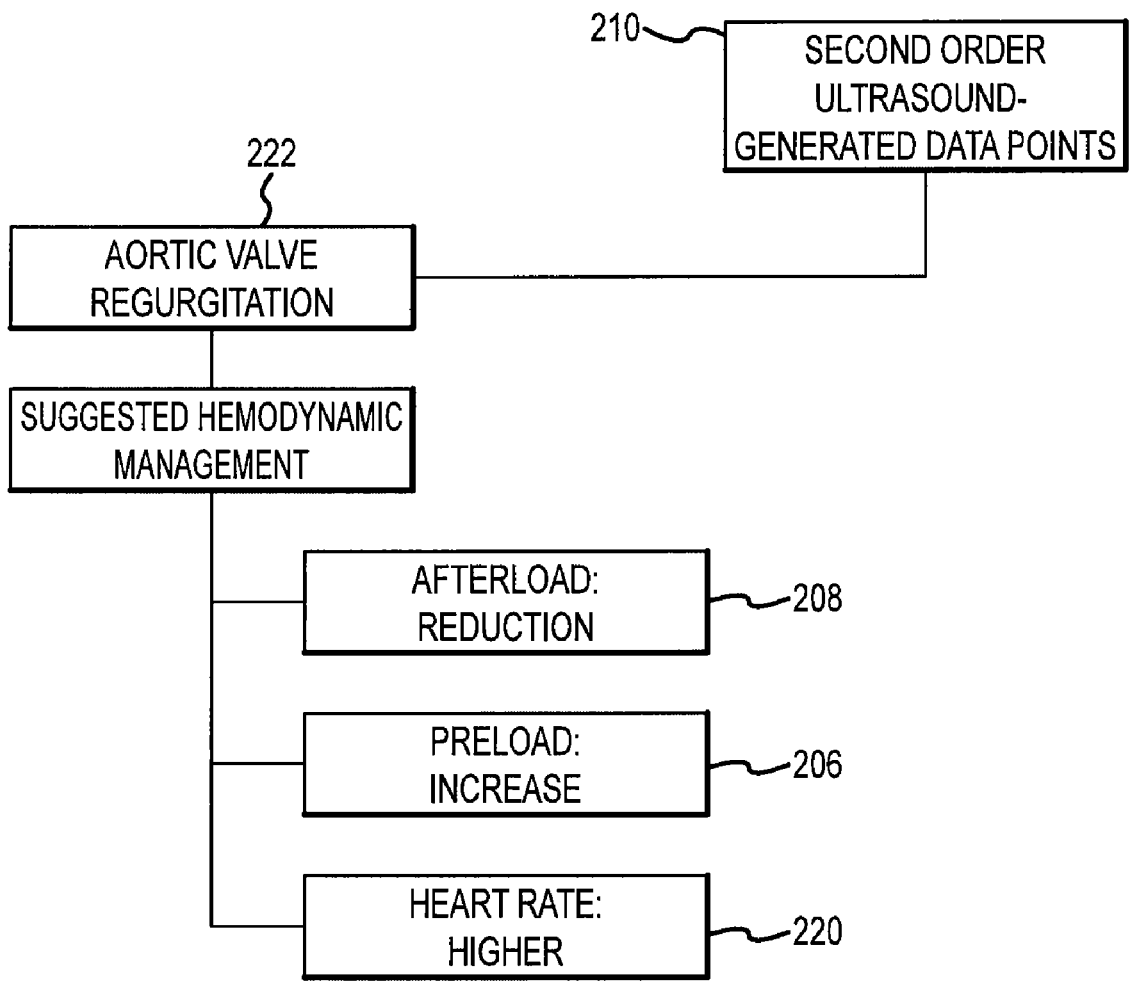
Figure 24:
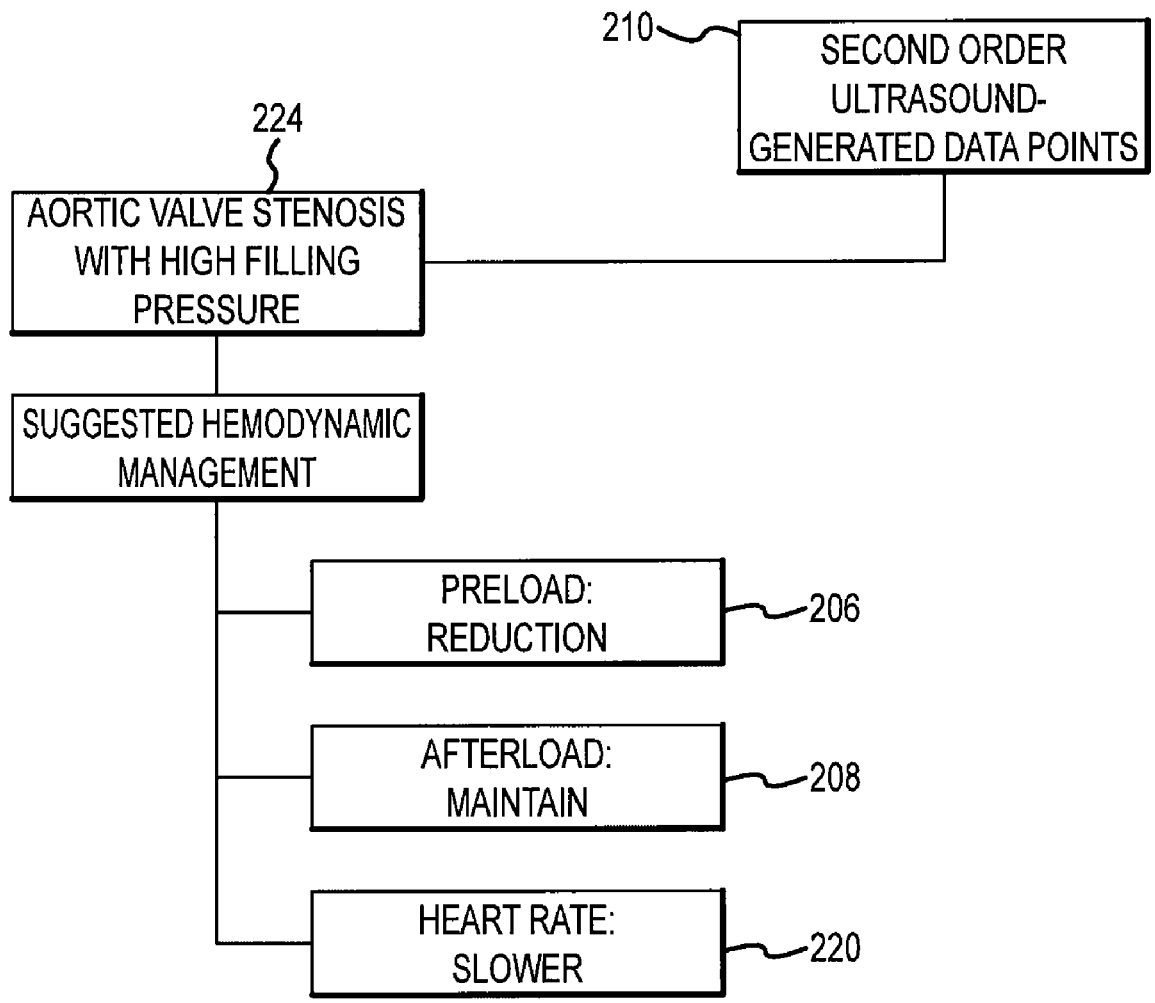
Figure 25:
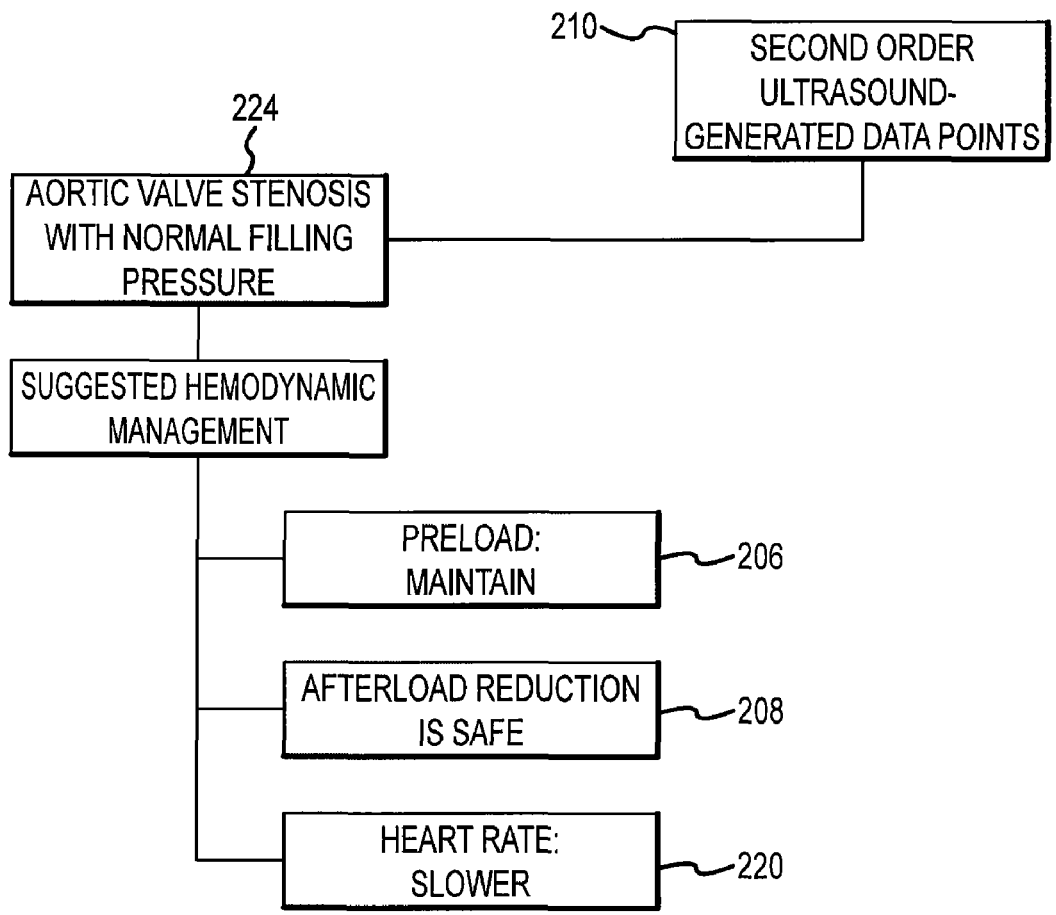

Referring now to FIG. 22, where the second order data points 210 indicate mitral valve regurgitation 216, the strategy may be to reduce the afterload 208 and maintain a faster heart rate 220 and higher preload 206 (Strategy 7). Where mitral valve stenosis 218 is indicated, the strategy may be to reduce the preload 206 and maintain a slower heart rate 220 (Strategy 7). Referring to FIG. 23, where the second order data points 210 indicate aortic valve regurgitation 222, the strategy may include reducing the afterload 208 and maintaining a faster heart rate 220 and higher preload 206 (Strategy 8). As shown in FIG. 24, in clinical cases where the second order data points 210 indicate aortic valve stenosis 224 with high filling pressures 204, the strategy may suggest to reduce the preload 206 and maintain a slower heart rate 220 (Strategy 9). As shown in FIG. 25, where the second order data points 210 indicate aortic valve stenosis 224 with normal filling pressures, the strategy may be to maintain a slower heart rate 220 and the module may also include an indication that afterload 208 reduction is safe (Strategy 10).

Figure 26:
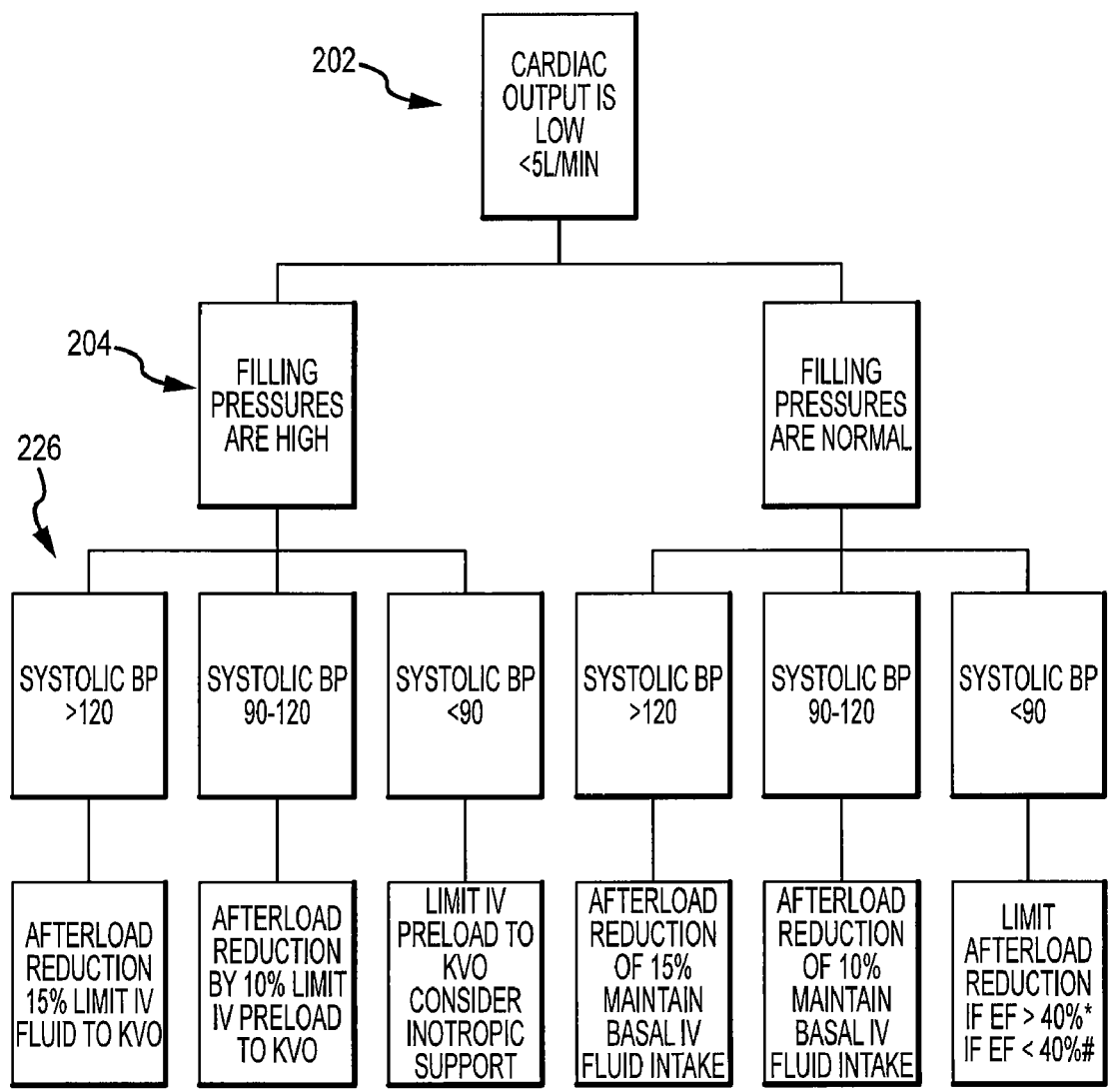
Figure 27:
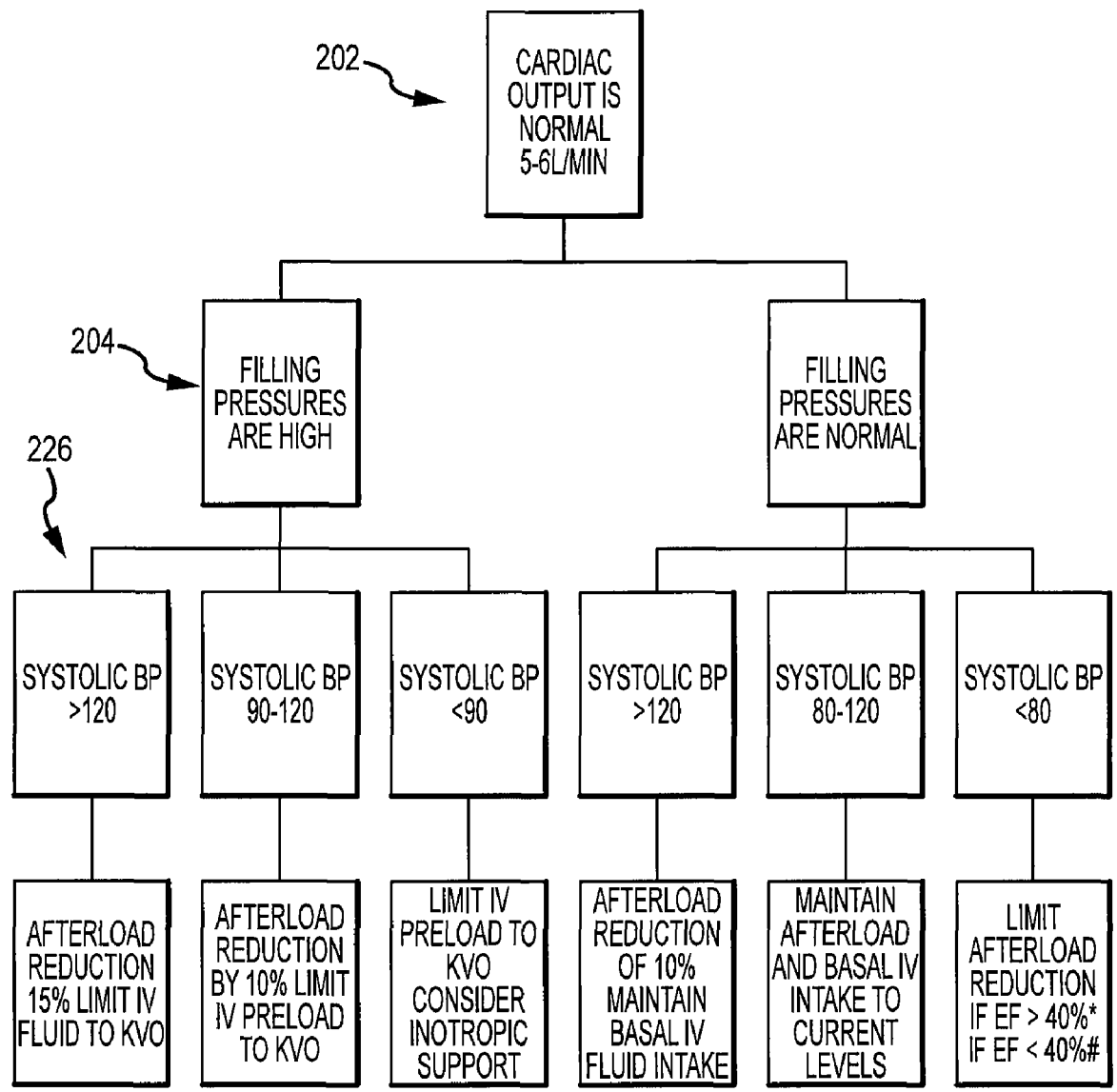

Referring now to FIGS. 26 and 27, clinical management strategies are shown with additional detail. Moreover, these strategies are shown to interface with a conventional parameter such as systolic blood pressure 226. With reference to FIG. 26, where the first order data points 200 indicate that the cardiac output 202 is low the clinical management module 140 can then look to the additional first order data point, filling pressure 204, to determine which of two branches to follow for determining a clinical strategy. Where the filling pressure 204 is high, three additional branches are based upon systolic blood pressure 226. For a systolic blood pressure (BP) 226 greater than 120 mm Hg, the clinical strategy may suggest reducing the afterload by 15% and limiting intravenous fluid (IV) as required to keep the vein opened (KVO). For a systolic BP 226 of 90 to 120 mm Hg, the clinical strategy may suggest reducing the afterload by 10% and limiting the IV preload to KVO. For a systolic BP 226 less than 90 mm Hg, the clinical strategy may suggest limiting the IV preload to KVO and to consider inotropic support. Similarly, where the filling pressures are normal, three additional branches also based on systolic BP 226 are shown. Where systolic BP 226 is greater than 120 mm Hg the clinical management strategy may be to reduce the afterload by 15% and maintain basal IV fluid intake. For a systolic BP 226 of 90 to 120 mm Hg, the clinical strategy may suggest to reduce the afterload by 10% and maintain basal IV fluid intake. Where systolic BP 226 is less than 90 mm Hg, the clinical strategy may suggest limiting the afterload reduction. A normal ejection fraction (EF) may be considered to be from 55% to 70% and in this case if the EF is greater than 40% the strategy may suggest that the provider consider an IV bolus of 250 ml. If the EF is less than 40%, the strategy may suggest that the provider consider inotropic support and if there is no increase or minimal increase in Stroke volume (SV), the strategy may further suggest that the provider consider an IV bolus of 100 ml.

A similar strategy to that shown in FIG. 26, is shown in FIG. 27 where the cardiac output 202 is normal. Here, the strategy differs from that shown in FIG. 26, in the normal filling pressure 204 branch. That is, in the normal filling pressure 204 branch, where the systolic BP 226 is greater than 120 mm Hg, the strategy suggests an afterload reduction of 10% in lieu of 15%. Also, for a systolic BP 226 of 90 to 120 mm Hg, the strategy suggests maintaining the afterload and the basal IV intake levels in lieu of reducing the afterload by 10% with maintained basal IV intake levels.

It is noted that the present disclosure is not to be limited to the specific percentages of reductions or increases shown and described. The reductions and increases in cardiovascular control determinants have been provided here as examples and do not reflect an exhaustive list of the available adjustments in the cardiovascular determinants. For example, the afterload reductions shown include reductions of 10% and 15%. The afterload reduction may range from approximately 0% to approximately 50% and preferably ranges from approximately 10% to approximately 20%. Additionally, in cases of sepsis or systemic infection, the afterload may be maintained or increased.

Additionally, the exemplary strategies shown are not an exhaustive list. For example, FIGS. 26 and 27 are based solely on cardiac output 202, filling pressure 204, and systolic BP 226. Other strategies can be included and can be based on any combination of cardiovascular determinants. The strategies can be further based on clinical experience and testing shown to bring cardiovascular functions closer to normal ranges.

The controller 102 can include an electronic reporting module 142. The electronic reporting module 142 can be adapted to facilitate the development of a report 145 for record keeping or other purposes. The report 145 compiled by the electronic reporting module 142 can include the clinical findings relating to patient condition and can also include the intervention measures taken to adjust, stabilize, or otherwise change the patient's condition. The electronic reporting module 142 can be adapted to prompt the provider with one or more report input screens 143 allowing the provider to select, confirm, modify, or otherwise tailor the report 145 and can also compile the report based on this input from the provider. The electronic reporting module 142 can be accessible via one or more of the input devices of the provider interface 104. That is, a menu button on the display 132 can be available for activating the electronic reporting module 142 and the menu button can be selected via a mouse, a touch screen, or any other input device. Other suitable activation elements and methods can be included such as a tab selection, a drop down box, and the like.

In a preferred embodiment, the electronic reporting module 142 can be adapted to compile an electronic and/or printed medical report. Preferably, the report 145 can include information relating to the hemodynamic management of a patient. Accordingly, as shown, for example in FIG. 28, the electronic reporting module 142 can prompt the provider with one or more report input screens 143. The screens 143 can prompt the provider for input relating to one or more of the clinical findings obtained by the analysis module 136 and/or intervention measures taken by the provider. The findings on any particular screen or screens 143 can include, the cardiac output, the filling pressures, the valvular structure and function, and the contractile function. Additionally, the screens can include intervention measures such as adjustments in the afterload, preload, heart rate, and contractility. Other findings or intervention measures can be included on the screens.

Figure 28:
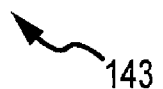
FIG. 28 is an exemplary report input screen for use in preparing a report.

As shown, in FIG. 28 for example, the report input screen 143 can be directed to the left-sided cardiac output. The screen may list a series of options suitable for the particular finding or intervention measure being addressed. Each of the options may include a short descriptive sentence representing a more detailed description of a clinical finding or an intervention measure. The selection of a report item can be in the form of radio buttons as shown or the selection can be check boxes, highlights, or other known selection types. The module 142 can be configured to allow only one selection or it can allow multiple selections for any given report item.

For each finding or intervention, the electronic reporting module 142 can make an initial selection for reporting based on information from the analysis module 136. That is, for example, if the analysis module 136 found that the LVOT was mildly decreased, the reporting module 142 can make an initial selection for confirmation or modification by the provider. If the provider has information indicating that the LVOT was something other than mildly decreased, the provider can select the appropriate finding. In the case of intervention measures, for example, if the clinical management module 140 suggested a preload reduction, the reporting module 142 may make an initial selection of preload reduction. However, if the actual intervention measure taken was not to adjust the preload, the provider can change the selection to, for example, maintain preload. In some embodiments, the module 142 can omit the initial selection and allow the provider to select the appropriate finding or intervention. It is noted, that the report input screens 143 can be directed to clinical findings or intervention measures not obtained or suggested, respectively, by the system. In these cases, the initial selection may be omitted. Where a common finding or intervention measure is known, the system can be configured to select the common finding or measure as a default for further review by the provider.

Upon selection or verification of the appropriate finding or intervention measure, the provider can be prompted to continue. Alternatively, the selection or verification can automatically cause the module to continue. The provider can be prompted with additional displays as required to select, verify, or otherwise obtain all of the necessary information for the report 145. Once complete, the electronic reporting module 142 can compile a suitable report 145. For example, as shown in FIG. 29, the report 145 can include the detailed descriptions of each of the clinical findings or intervention measures taken and can also include a summary of the procedures.

The compiled report 145 can be in electronic form in a database report format, a word processing format, or another format. The report 145 can be saved, printed, or otherwise stored as a record. The report 145 can be formatted to comply with the medical record bylaws of a particular healthcare facility or series of facilities. In addition, the report 145 may be electronically coded according to Hospital Language (HL) protocol and sent out as a patient electronic medical record in a compatible format.

The controller 102 can include a DRG module 144. Many healthcare system revenues are determined by the Diagnosis Related Group (DRG) billing codes resulting from a patient's visit to their facilities. Each DRG code can be associated with a specific fee for which the hospital can be reimbursed relating to a specific rendered healthcare service. Most DRG codes have two formats: a basic DRG and a DRG with complications and comorbidities (CCs). DRG codes associated with clearly documented CCs are typically reimbursed at a higher rate than those without CCs (i.e., a basic DRG). In the event that CCs are adequately identified and documented, reimbursement at the higher, DRG with CCs, rate is possible. In addition, identification of CCs at the time of admission of the patient to the healthcare facility allows for the documentation of cardiac comorbidities as Present On Admission (POA), as opposed to a post-operative complication diagnosis. This may reduce the likelihood of lower reimbursement that is now tied to the pay-for-performance Medicare and other insurance carrier programs. The device described herein allows identification of cardiovascular complications and comorbidities and as such may allow for early identification of conditions and thus a higher rate of reimbursement.

Figure 31:
FIG. 31 is an exemplary DRG report.

The DRG module 144 may allow for the documentation of identified CCs. When activated by the healthcare provider, the DRG module 144 may display a list of International Classification Diseases (ICD) codes describing cardiovascular CCs capable of being identified by the device. This list may be displayed on the display 132 as described above and as shown, by way of example, in FIG. 30. By selecting the most appropriate diagnosis (ICD codes) identified by the device, the end-user may generate a series of billing codes that may be used by the healthcare facility to document the CCs. The billing codes may be documented in a separate report called the DRG optimization report 147 as exemplified in FIG. 31. The report 147 may be printed on paper or written in an electronic document. The report 147 may be added to the patient paper or electronic medical record. The report 147 may also be sent by paper and or electronically to the healthcare facility billing and coding department as a separate document from the medical record. This report 147 may improve the capture of reimbursement for CCs by the healthcare facility billers and coders for optimization of the patient's final DRG code submitted to the insurance company for the services rendered. The billing codes generated may also be used in a separate document called a professional billing claim 149 as shown, by way of example, in FIG. 32. This document may allow for the healthcare provider to be paid for the professional services rendered with use of the device according to the Current Procedural Terminology (CPT) code fee schedule.

Referring now to FIGS. 33-36, the system methodology may be described. The system can function to acquire data from patients for use in managing the patient's condition and may further be used as a reporting tool. Using the patient interface 100, the system may be adapted to obtain patient information relevant to a particular procedure or condition. The system can be further adapted to analyze and/or display that information. In addition, the system can suggest a suitable clinical strategy for managing the condition of the patient.

In a preferred embodiment, the probes 110 of the preferred patient interface 100 described, can be used to obtain cardiovascular function information from a patient. The probes 110 may obtain information based upon their position on the patient. That is, certain positions can represent a cardiovascular window as described above and can lend themselves toward collection of particular items of cardiovascular information. Accordingly, in a preferred embodiment, each probe 110 may have a particular set of data collection allocated to it based on the particular window it is positioned in. However, depending on patient anatomy and other factors, a probe 110 in any given position may not be able to access the information typically available from its respective position. In these cases, other positions can be used to compile the most complete set of data available.

More particularly, in a preferred embodiment, the basic sequence of data acquisition may occur through the use of two probes 110. That is, in some embodiments, two probes 110 may be able to collect all of the cardiovascular function information by allocating some of the information to a first probe 110 and the remaining information to the second probe 110. In other embodiments, two probes 110 may not be sufficient due to obstructions or other intervening causes. In still other embodiments, additional probes 110 may be used to get additional information by viewing particular structures from additional views. In some embodiments, a single probe 110 may be sufficient. In other embodiments, any number of probes 110 may be used.

Figure 33:
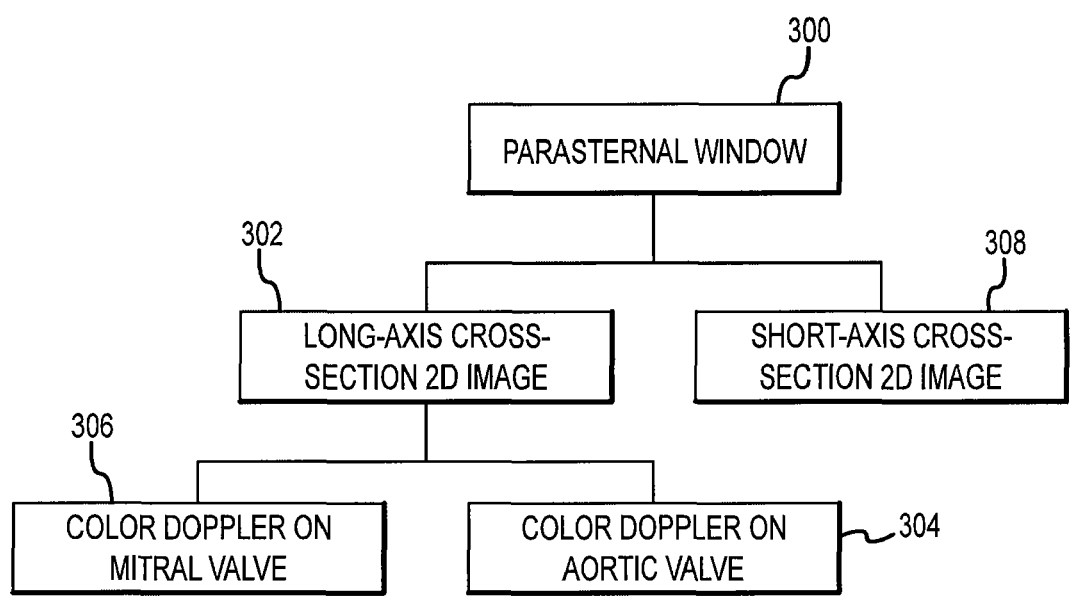
FIGS. 33-36 are each charts reflecting steps taken to obtain patient information according to certain embodiments.

Referring to FIG. 33, in a preferred embodiment, a first probe 110 can be secured on a patient's chest at the parasternal window 300. This probe 110 may be set by the patient interface module 134 to a first mode for a 2D black and white image. The patient interface module 134 can adjust the probe 110 to acquire a parasternal long-axis 2D imaging cross-section 302 of the heart for one or more heart beats. This black and white 2D image clip can show the left ventricular heart muscle contracting and the mitral and aortic valves open and close. From the same 2D cross-section, for example, without adjusting the view of the probe 110, the mode of the first probe 110 can be changed to a second mode and a color Doppler ROI box may be superimposed on the aortic 304 and mitral 306 valves 2D live image. A clip of the data may be acquired for one or more heart beats. The color Doppler allows the assessment of the valves functionality by revealing the blood flow through the valves. Still using the first probe 110, additional data may be acquired by adjusting the probe 110 from the parasternal long-axis 2D imaging cross-section 302 to a parasternal short-axis 2D imaging cross-section 308 for one or more heart beats. This short-axis probe view 308 can allow for the assessment of the left ventricular contractile function and volume status.

Figure 34:
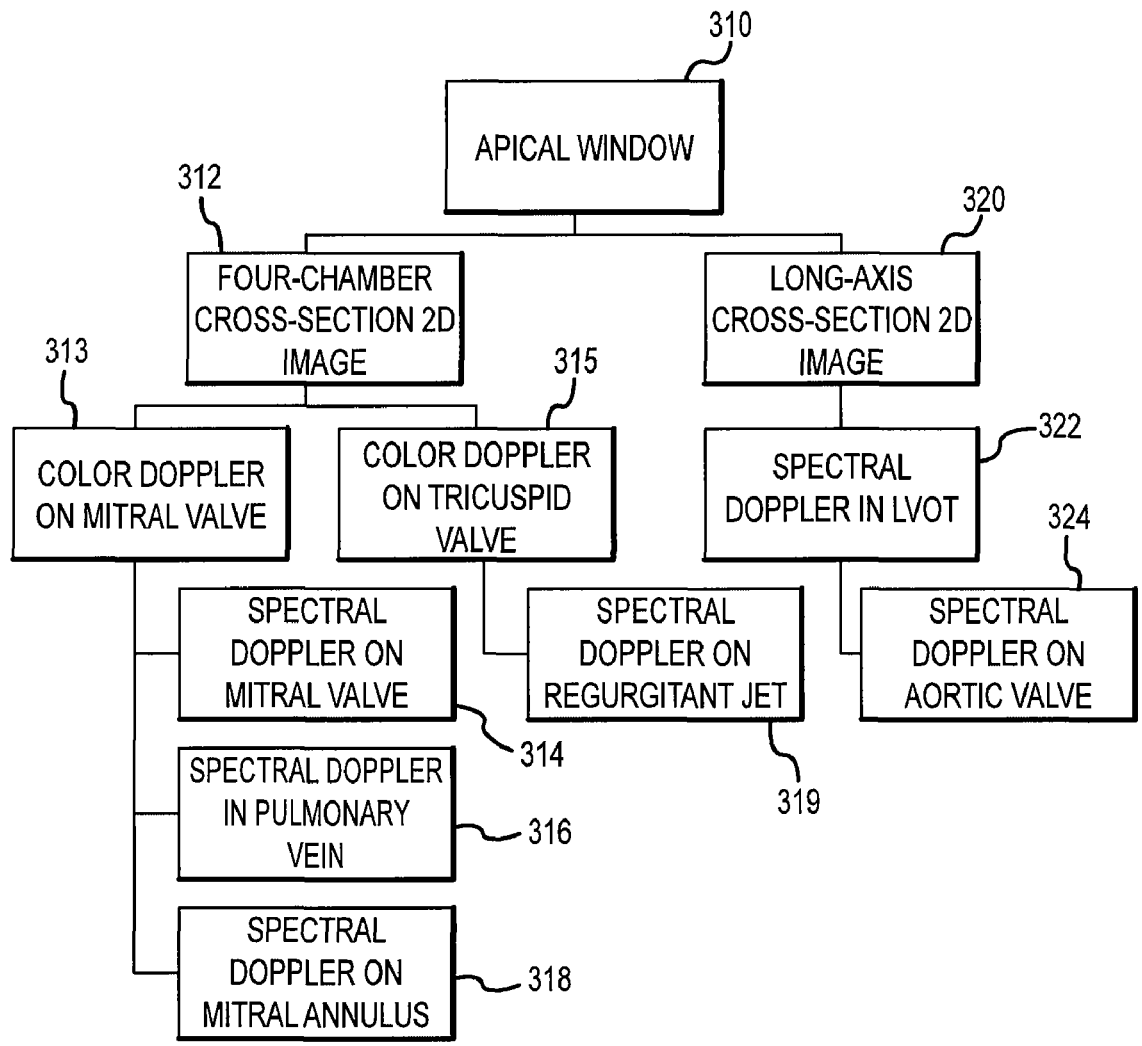

Referring to FIG. 34, in a preferred embodiment, a second probe 110 can be secured on the patient's chest at the apical window. This second probe 110 can be set by the patient interface module 134 to a first mode for a 2D black and white image. The patient interface module 134 can adjust the second probe 110 to acquire an apical four-chamber 2D imaging cross-section 312 for one or more heart beats. This 2D clip can evaluate the right and left ventricular contractile function, as well as the mitral and tricuspid valve. This additional 2D clip allows for the three-dimensional heart structure to be assessed by a series of two-dimensional cross-sections by relying on view from several angles. The probe 110 can be set to a second mode for a color Doppler image of the mitral 313 and triscuspid valve 315. From the same 2D cross-section, for example, without adjusting the view of the probe 110, the mode of the first probe 110 can be changed to the third mode and a pulsed-wave spectral Doppler ROI box may be superimposed on the open mitral valve 314 to measure the velocity of the red cells coming into the heart during diastole. The data may be acquired and displayed on a spectral graph showing velocity over time. The same pulsed-wave spectral Doppler ROI box, for example, without changing the size of the ROI box, may be superimposed on the right upper pulmonary vein 316. The velocity/time spectral graph of the pulmonary venous flow may then be acquired. The pulsed-wave spectral Doppler ROI box may also be superimposed on the septal or lateral side of the mitral valve annulus 318 to measure the tissue Doppler velocities of the left ventricle. Those three spectral Doppler measurements may then be used to assess the left ventricular diastolic function and filling pressure. Also, a continuous wave Doppler sampling of the tricuspid regurgitation jet 319 peak velocity may be made to estimate the right ventricular/pulmonary artery pulmonary pressure.

In a preferred embodiment, the patient interface module 134 can set the second probe 110 back to mode 1 and adjust the second probe 110 to acquire a 2D cross-section called an apical long-axis 320 for one or more heart beats. From the same apical long-axis 2D cross-section, patient interface module 134 can set the second probe 110 to the 3rd mode and a pulsed-wave spectral Doppler sampling area may be superimposed on the left ventricular outflow tract (LVOT) 322 to measure the velocity of the red cells being ejected out of the left heart over a cardiac cycle (left-sided cardiac output). Additionally, a continuous-wave spectral Doppler may be directed in the same longitudinal axis to measure the velocity of the red cells at the level of the aortic valve 324. This additional velocity allows the evaluation and quantification of aortic valve stenosis.

Figure 35:
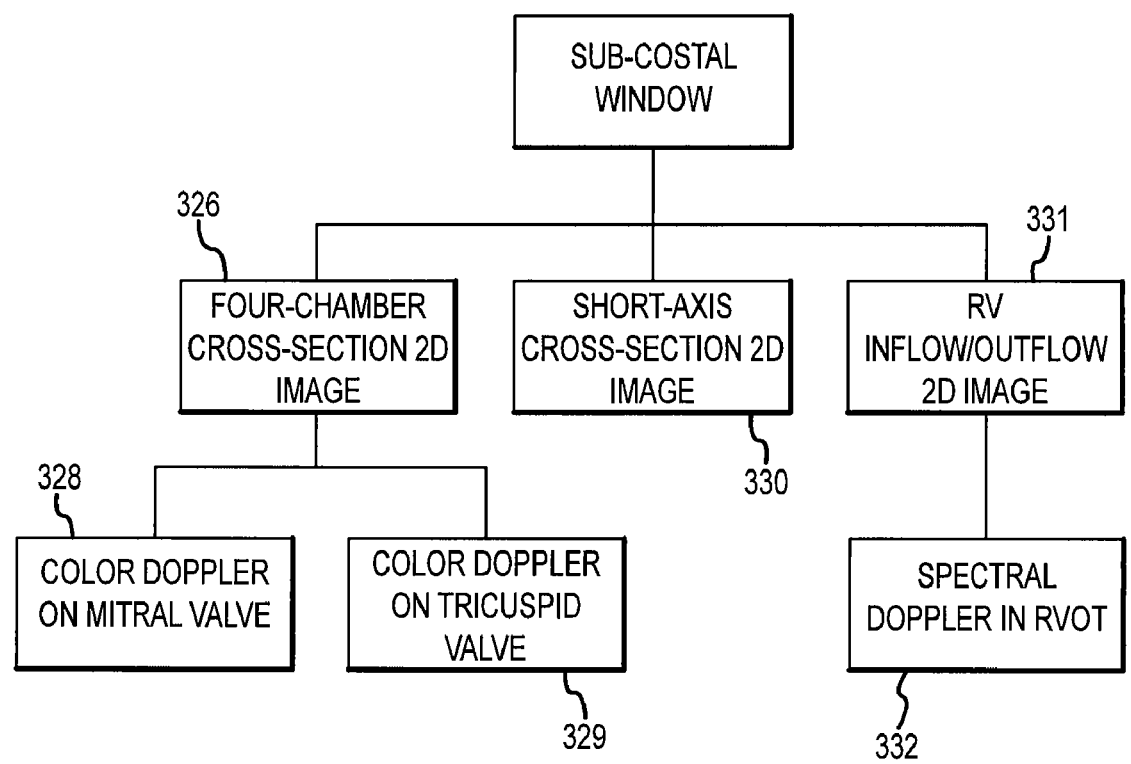

As mentioned, in some embodiments, the information gathered from the first and second probes 110 may be insufficient due to obstructed views or other intervening causes or additional views may be desired. Referring to FIG. 35, in some embodiments, a third probe 110 can be secured on the patient's upper abdomen under the right costal ridge in the sub-costal window. The patient interface module 134 can set the third probe 110 to a first mode for a 2D black and white image. The patient interface module 134 can adjust the third probe 110 to acquire a sub-costal four chamber 2D imaging cross-section 326 for one or more heart beats. This 2D clip may evaluate the right and left ventricular contractile function, the size of the inferior vena cava as well as the mitral and tricuspid valve. From the same 2D cross-section, the patient interface module 134 can set the third probe 110 to a second mode and a color Doppler region of interest (ROI) box may be superimposed on the mitral valve 328 and the tricuspid valve 329. A clip of the data may be acquired for one or more heart beats. The color Doppler can allow the assessment of the mitral and tricuspid valve functionality. In the present embodiment, and still using the third probe 110, the patient interface module 134 can set the third probe 110 to a first mode. The third probe 110 can be adjusted for a sub-costal right ventricular inflow-outflow 2D imaging cross-section 331, which may be acquired for one or more heart beats. This allows the evaluation of the right heart structures and function. From the same 2D cross-section, the patient interface module 134 can set the third probe 110 to a third mode and a pulsed-wave spectral Doppler sampling area may be superimposed on the right ventricular outflow tract (RVOT) 332 to measure the velocity of the red cells being ejected out of the right heart over a cardiac cycle (right-sided cardiac output). Still using the third probe 110, a sub-costal LV short-axis 2D imaging cross-section 330 may be acquired for one or more heart beats. This allows the assessment of the left ventricular contractile function and volume status.

When the ultrasound-generated data points from the second probe 110 regarding the left heart cardiac output are inadequate or when additional views are desired, the user may rely on a fourth probe 110 to acquire a continuous-wave spectral Doppler tracing signal of either the ascending aorta or the distal aortic arch or the descending aorta.

Figure 36:
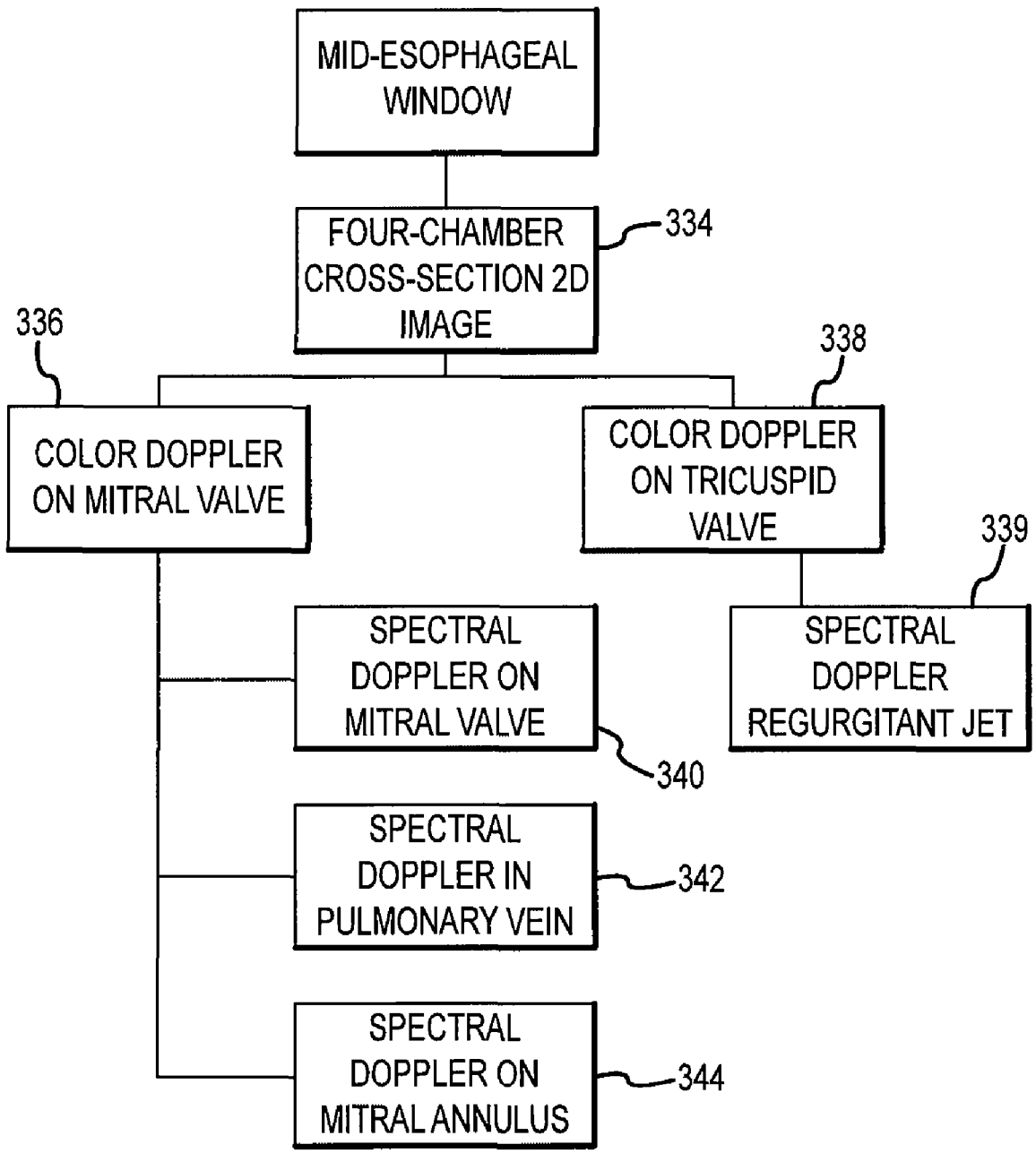

When the ultrasound-generated data points from the first, second, third, or fourth probes 110 are inadequate or as an additional available set of data, a fifth probe 110 can be used. Referring to FIG. 36, the fifth probe 110 may be positioned in the mid-esophageal window and may acquire ultrasound-generated data points from behind the heart (inside the body). The fifth probe 110 may acquire a mid-esophageal four chamber 2D imaging cross-section 334 for one or more heart beats. This 2D clip evaluates the right and left ventricular contractile function, as well as the mitral and tricuspid valves. From the same 2D cross-section, a color Doppler region of interest (ROI) box may be superimposed on the mitral 336 and tricuspid 338 valves 2D live image. A clip of the data may also be acquired for one or more heart beats. The color Doppler allows the assessment of the mitral and tricuspid valve functionality. From the same 2D cross-section, a pulsed-wave spectral Doppler sampling area may be superimposed on the opened mitral valve 340 to measure the velocity of the red cells coming into the heart during diastole. The data may be acquired and displayed on a spectral graph showing velocity over time. Then, the same pulsed-wave spectral Doppler sampling area may be superimposed on the left upper pulmonary vein 342. The velocity/time spectral graph of the pulmonary venous flow may then be acquired. The pulsed-wave sampling Doppler may then be superimposed on the septal or lateral side of the mitral valve annulus 344 and may measure the tissue Doppler velocities of the left ventricle. Those three spectral Doppler measurements may be used to assess the left ventricular diastolic function and filling pressure. A continuous wave Doppler sampling of the tricuspid regurgitation jet 339 peak velocity may be made to estimate the right ventricular/pulmonary artery pulmonary pressure.

The method resulting from the use of the described device may be referred to as Echocardiography-Guided Anesthesia Management (EGAM) and/or Echocardiography-Guided Hemodynamic Management (EGHEM). EGAM/EGHEM may automatically acquire ultrasound-generated real-time data points like cardiac output and filling pressures to assess, manage, modify and optimize the patient cardiac preload, afterload, heart rate and contractility. Two clinical case studies were conducted as described below.

Clinical Example 1

Step 1: Patient Selection

Male patient, 81 year old, scheduled for a left hip pinning for a fracture repair. He weighs 89 Kg and is 178 cm tall. His BSA is 2.1 m2. The patient has long-standing hypertension, and has a history of transmural myocardial infarction (MI) 4 years prior. The patient has a limited functional capacity of approximately 5 METs with symptoms of shortness of breath (SOB), occasional chest pain stable for last two years, and hip pain. His medication includes an ACEI and a beta-blocker.

Step 2: Baseline Pre-Operative Assessment

The device and methods previously described in this document were applied to this patient. This process was performed at bedside before anesthesia was provided. The process was pain free and took a few minutes to complete. Below is the summary of the information provided by the device:
Baseline vital signs:
 a. blood pressure (BP)=160/85 mmHg,
 b. heart rate (HR)=82 bpm, regular,
 c. $SpO_2$=92% room air.
Primary EGAM/EGEM findings:
 a) Reduced cardiac output: LVOT diameter is 2 cm, LVOT VTI=12 cm. CO: 3.1 L/min, CI=1.5 L/min/m$^2$
 b) LV Filling pressures are elevated based on a pseudonormal LV filling pattern, a pulmonary venous flow diastolic dominant and an E/e' ratio of 25.
Secondary EGAM/EGHEM findings;
 a) Mitral valve: mild regurgitation.
 b) Aortic valve: sclerosis without significant stenosis.
 c) LV contractile function: moderately reduced with a visually estimated ejection fraction (EF) at 30%.

Step 3: Management Strategies

The patient presents a low cardiac output, high filling pressure, high systemic blood pressure, reduced LV contractile function and mild mitral regurgitation. The suggested EGAM/EGHEM strategy based on FIG. 26 recommendation is to reduce the afterload and blood pressure by 15% and limit all IV intakes only to keep the vein open. A general anesthetic is planned with IV induction agents and maintenance done with an inhalational agent. If required, the basal IV intake needs are 65 ml/hour. The EGAM/EGHEM data will be controlled 5 minutes after induction.

Step 4: Ongoing Intra-Operative Assessment

The following table summarizes the intra-operative findings and interventions

| Timeline | Cardiac output | Filling pressure | Blood pressure | LV contractility | Interventions |
| --- | --- | --- | --- | --- | --- |
| Baseline | 3.1 L/min | High E/e' = 25 | 160/85 | EF = 30% | Limit preload Reduce to systolic BP to 136 |
| 5 min post-induction | 3.5 L/min | High E/e' = 20 | 132/78 | No change | Limit preload Reduce BP to 112 |
| Control #1 15 min later | 3.8 L/min | Normal E/e' = 13 | 108/72 | Mild increase | Maintain basal needs Reduce BP to 98 |
| Control # 2 15 min later | 4.2 L/min | Normal E/e' = 12 | 96/68 | No change | Maintain basal needs Reduce BP to 90 |

-continued

| Timeline | Cardiac output | Filling pressure | Blood pressure | LV contractility | Interventions |
|---|---|---|---|---|---|
| Control # 3 7 min later | 4.4 L/min | Normal E/e' = 10 | 84/62 | EF = 35% | Give IV bolus 100 ml Limit afterload reduction |
| Control # 4 5 min later | 4.5 L/min | Normal E/e' = 14 | 92/64 | No change | Maintain basal needs Maintain afterload |
| Control # 5 15 min later | 4.3 L/min | Normal E/e' = 12 | 96/68 | No change | Maintain basal needs Maintain afterload |
| Control # 6 In recovery room | 3.8 L/min | Normal E/e' = 14 | 145/72 | No change | Maintain basal needs Reduce BP to low 90's |

Follow-Up Events

The case lasted for about 1 hour. The patient received a total of 250 ml of IV fluid. The urine output during the procedure was 150 ml. The blood loss was estimated at 150 ml. The SpO2 on room air in recovery room as well as post-op day 1 was 98%. The patient remained comfortable. The post-operative course included an increase of blood pressure medication and the addition of a low dose diuretic, as well as a reduced salt and fluid intake. The target systolic BP was in the 90's. The discharge weight was 83 kg, the CO was 4.3 L/min, BP=96/72. The patient tolerated those changes well and reported no orthostatic hypotension, no stroke, and no changes of renal function. He was still alive and doing well at 30 days post-op and did not require readmission during the same period and had no new cardiac events.

The device effectively identified that the patient was in a non compensated state of congestive heart failure with reduced cardiac output and ventricular contractility. The clinical strategy used to address those issues was significantly different than what the standard pre-operative evaluation was dictating because the supplemental information provided by the device suggested a completely opposite strategy. By using the invention, the health care provider had access to more accurate information, was able to provide better care to the patient and reduce the risk of post-operative cardiovascular complications.

Case Study 2

Step 1: Patient Selection

Female patient, 82 year old, scheduled for elective, right hemicolectomy. She weights 79 Kg and is 160 cm tall. Her BSA is 1.9 m2. Patient has medically treated hypertension with a hydrochlorothiazide. She stopped smoking two year ago but has a 20 pack-years history. She is complaining of a progressive shortness of breath and reduction of her functional capacity over the last year, currently estimated at 6 or 7 METs. She has no chest pain or palpitations.

Step 2: The Baseline Pre-Op Assessment

The device and methods previously described in this document were applied to this patient. This process was performed at bedside before anesthesia was provided. The process was pain free and took a few minutes to complete. Below is the summary of the information provided by the device:

Baseline vital signs:
  a. blood pressure (BP)=168/92 mmHg,
  b. heart rate (HR)=70 bpm, regular,
  c. $SpO_2$=90% room air.

Primary EGAM/EGHEM findings:
  a) Normal cardiac output: LVOT diameter is 2 cm, LVOT VTI=22 cm. CO: 4.8 L/min, CI=2.5 L/min/m$^2$
  b) LV Filling pressures are elevated based on a restrictive filling pattern, a pulmonary venous flow diastolic dominant and an E/e' ratio of 35.

Secondary EGAM/EGHEM findings:
  a) Mitral valve: mild to moderate regurgitation.
  b) Aortic valve: sclerosis with mild stenosis.
  c) LV contractile function is normal with a visually estimated EF at 60%

Step 3: Management Strategies

The patient presents a normal cardiac output, high filling pressure, high systemic blood pressure, a normal LV contractile function, mild to moderate mitral regurgitation and mild aortic stenosis. The suggested EGAM/EGHEM strategy based on FIG. 27 is to reduce the afterload and blood pressure by 15% and limit all IV intakes only to keep the vein open. A general anesthetic is planned with IV induction agents and maintenance done with total intravenous anesthetics agents. If required, the basal IV intake needs are 60 ml/hour. The EGAM/EGHEM data will be controlled 5 minutes after induction.

Step 4: Ongoing Intra-Operative Assessment

The following table summarizes the intra-operative findings and interventions

| Timeline | Cardiac output | Filling pressure | Blood pressure | LV contractility | Interventions |
|---|---|---|---|---|---|
| Baseline | 4.8 L/min | High E/e' = 35 | 162/92 | EF = 60% | Limit preload Reduce to systolic BP to 145 |
| 5 min post-induction | 5.1 L/min | High E/e' = 30 | 141/72 | No change | Limit preload Reduce BP to 120 |

-continued

| Timeline | Cardiac output | Filling pressure | Blood pressure | LV contractility | Interventions |
|---|---|---|---|---|---|
| Control #1<br>15 min later | 5.5 L/min | High<br>E/e' = 26 | 128/67 | No change | Limit preload<br>Reduce BP to 110 |
| Control # 2<br>15 min later | 5.3 L/min | High<br>E/e' = 24 | 105/59 | No change | Limit preload<br>Reduce BP to 95 |
| Control # 3<br>15 min later | 5.4 L/min | High<br>E/e' = 22 | 92/55 | No change | Limit preload<br>Maintain afterload |
| Control # 4<br>15 min later | 5.2 L/min | Normal<br>E/e' = 14 | 96/58 | No change | Maintain basal needs<br>Maintain afterload |
| Control # 5<br>15 min later | 5.3 L/min | Normal<br>E/e' = 12 | 98/64 | No change | Maintain basal needs<br>Maintain afterload |
| Control # 6<br>15 min later | 4.8 L/min | Normal<br>E/e' = 10 | 78/48 | No change | Give IV bolus of 250 ml<br>Maintain afterload |
| Control # 7<br>In recovery room | 5.1 L/min | Normal<br>E/e' = 14 | 105/74 | No change | Maintain basal needs<br>Reduce BP to 90's |

Follow-Up Events

The case lasted for about 2 hours. The patient received a total of 300 ml of IV fluid. The urine output during the procedure was 450 ml. The blood loss was estimated at 250 ml. The SpO2 on room air in recovery room was 97%. The patient remained comfortable. The post-operative course included an increase of his existing blood pressure medication and the addition of an ACEI, as well as low sodium diet. The target systolic BP was in the 90's. The discharge weight was 72 kg, the CO was 5.2 L/min, BP=100/68. The patient tolerated those changes well and reported no orthostatic hypotension, no stroke, and no changes of renal function. She was still alive and doing well at 30 days post-op and did not require readmission during the same period and no new cardiac events.

The device effectively identified that the patient was in a non compensated state of congestive heart failure with normal cardiac output and ventricular contractility but very high filling pressures. The clinical strategy used to address those issues was significantly different than what the standard pre-operative evaluation was dictating because the supplemental information provided by the device suggested a completely opposite strategy. By using the invention, the health care provider had access to more accurate information, was able to provide better care to the patient and reduce the risk of post-operative cardiovascular complications.

As shown and described regarding FIGS. 37-42, the system may perform several methods. The steps included in any of the described methods may be completed in any order and any or all of the steps may be included.

Figure 37:
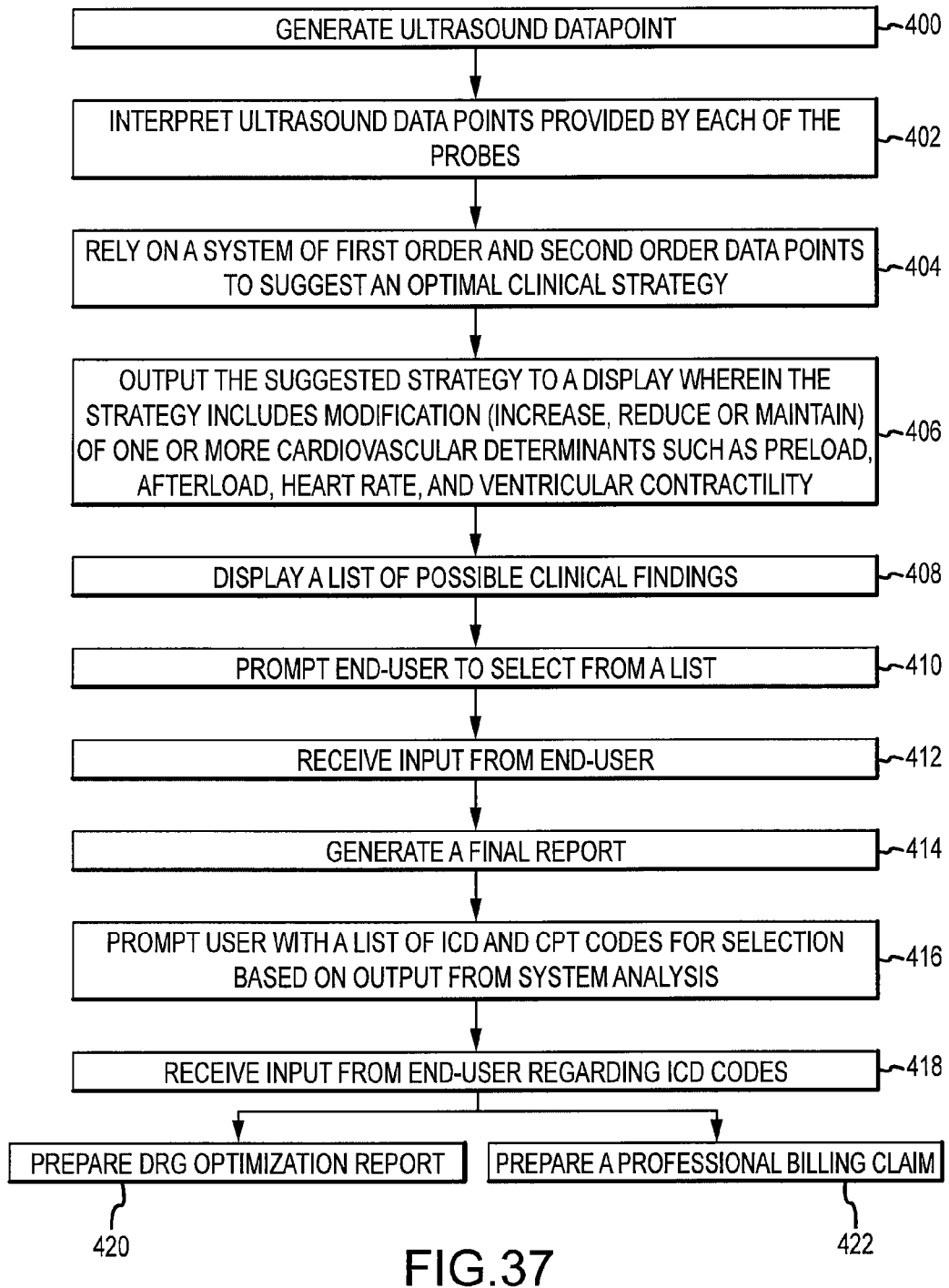
FIG. 37 is a chart showing steps taken by a hemodynamic management system to assist in managing a patient according to certain embodiments.

Referring to FIG. 37, a method of is shown including at box 400, Generate ultrasound data point, at box 402, Interpret ultrasound data points provided by each of the probes 10, at box 404, Rely on a system of first order and second order data points to suggest an optimal clinical strategy, at box 406, Output the suggested strategy to a display wherein the strategy includes modification (increase, reduce or maintain) of one or more cardiovascular determinants such as preload, afterload, heart rate, and ventricular contractility, at box 408, Display a list of possible clinical findings, at box 410, Prompt end-user to select from a list, at box 412, Receive input from end-user, and at box 414, Generate a Final Report.

In addition, the method may include at box 416, Prompt user with a list of ICD codes for selection based on output from system analysis, at box 418, Receive input from end-user regarding ICD codes, at box 420, Prepare DRG optimization report, and at box 422, prepare a professional billing claim.

Figure 38:
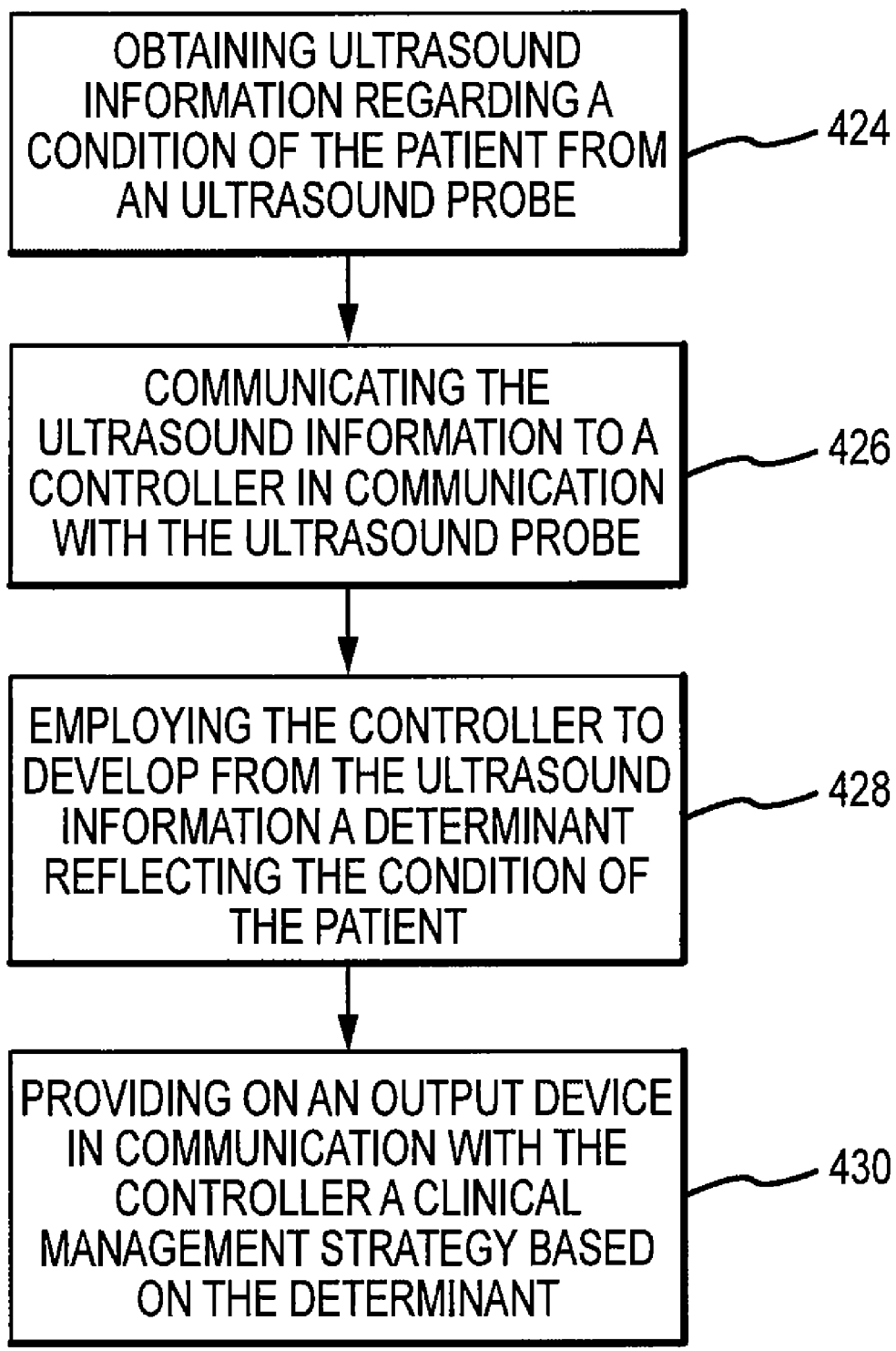
FIG. 38 is a chart showing a method of presenting a clinical management strategy for a patient.

Referring to FIG. 38, a method is shown including, at box 424, obtaining ultrasound information regarding a condition of the patient from an ultrasound probe, at box 426, communicating the ultrasound information to a controller in communication with the ultrasound probe, at box 428, employing the controller to develop a determinant from the ultrasound information reflecting the condition of the patient, and at box 430, providing on an output device in communication with the controller a clinical management strategy based on the determinant.

Figure 39:
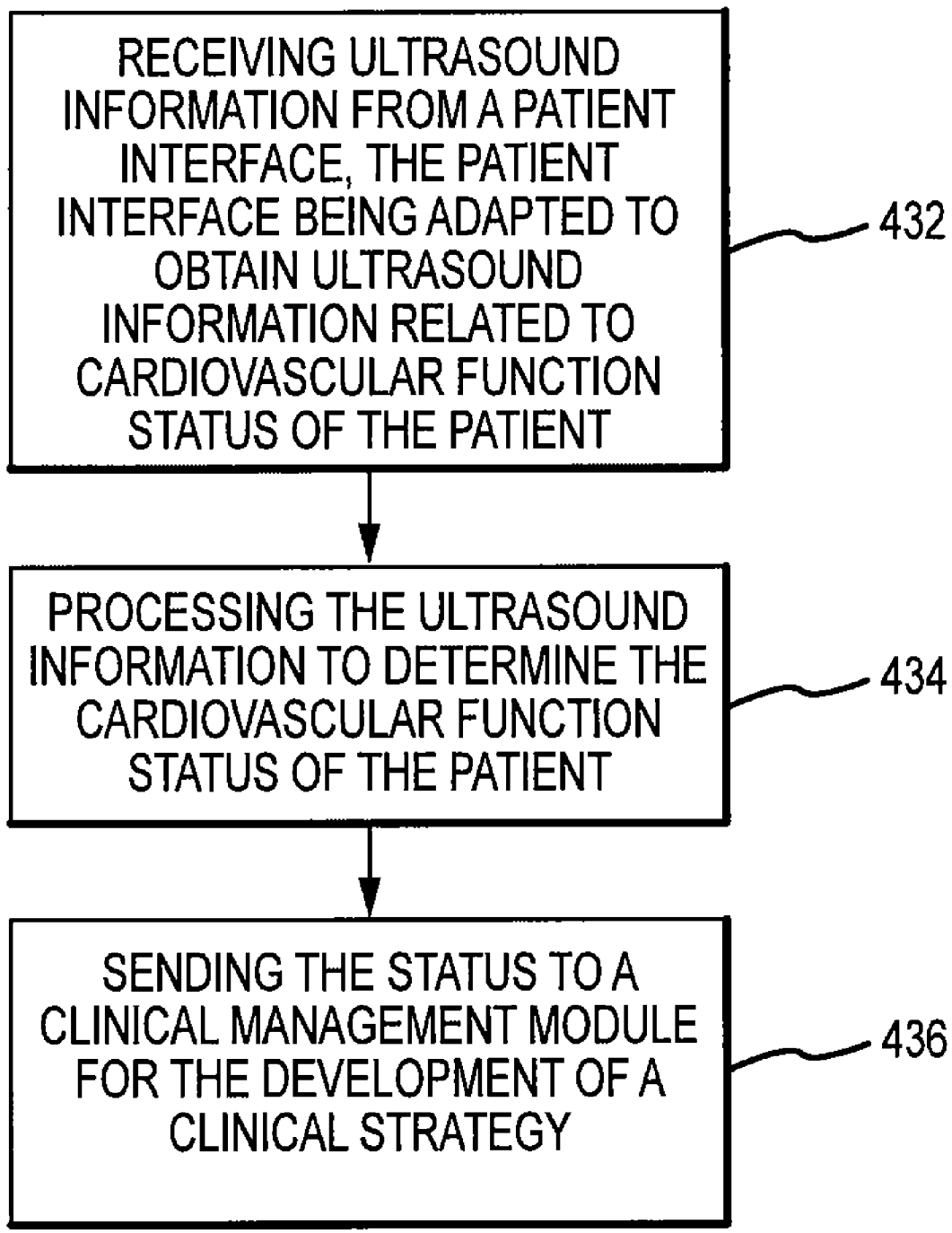
FIG. 39 is a chart showing a method of developing a cardiovascular determinant of a patient.

Referring to FIG. 39, a method is shown including, at box 432, receiving ultrasound information from a patient interface, the patient interface being adapted to obtain ultrasound information related to cardiovascular function status of the patient, at box 434, processing the ultrasound information to determine the cardiovascular function status of the patient, and at box 436, sending the status to a clinical management module for the development of a clinical strategy.

Figure 40:
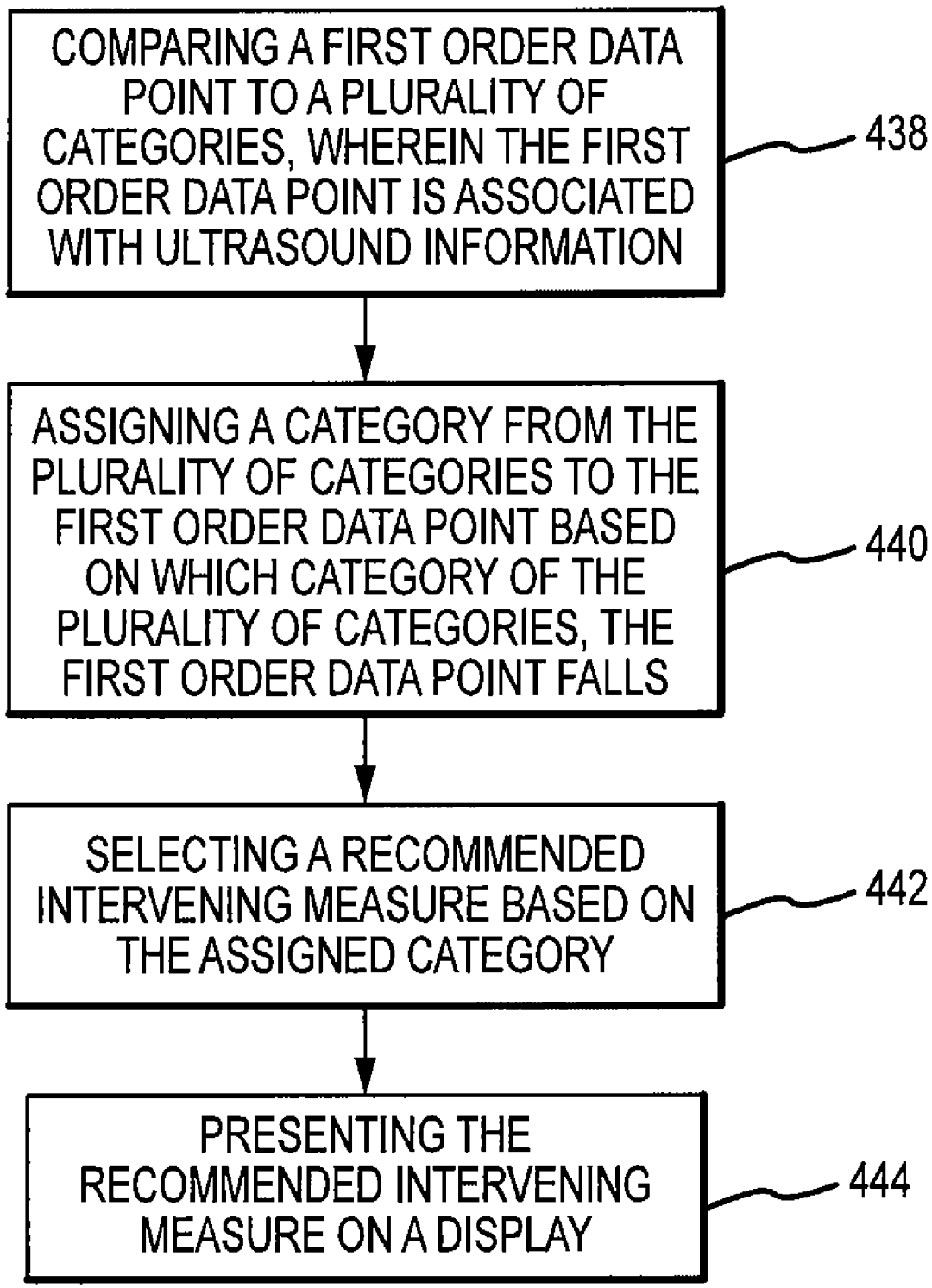
FIG. 40 is a chart showing a method of suggesting a clinical management strategy.

Referring to FIG. 40, a method is shown including, at box 438, comparing a first order data point to a plurality of categories, wherein the first order data point is associated with ultrasound information, at box 440, assigning a category from the plurality of categories to the first order data point based on which category of the plurality of categories, the first order data point falls, at box 442, selecting a recommended intervening measure based on the assigned category, and at box 444, presenting the recommended intervening measure on a display.

Figure 41:
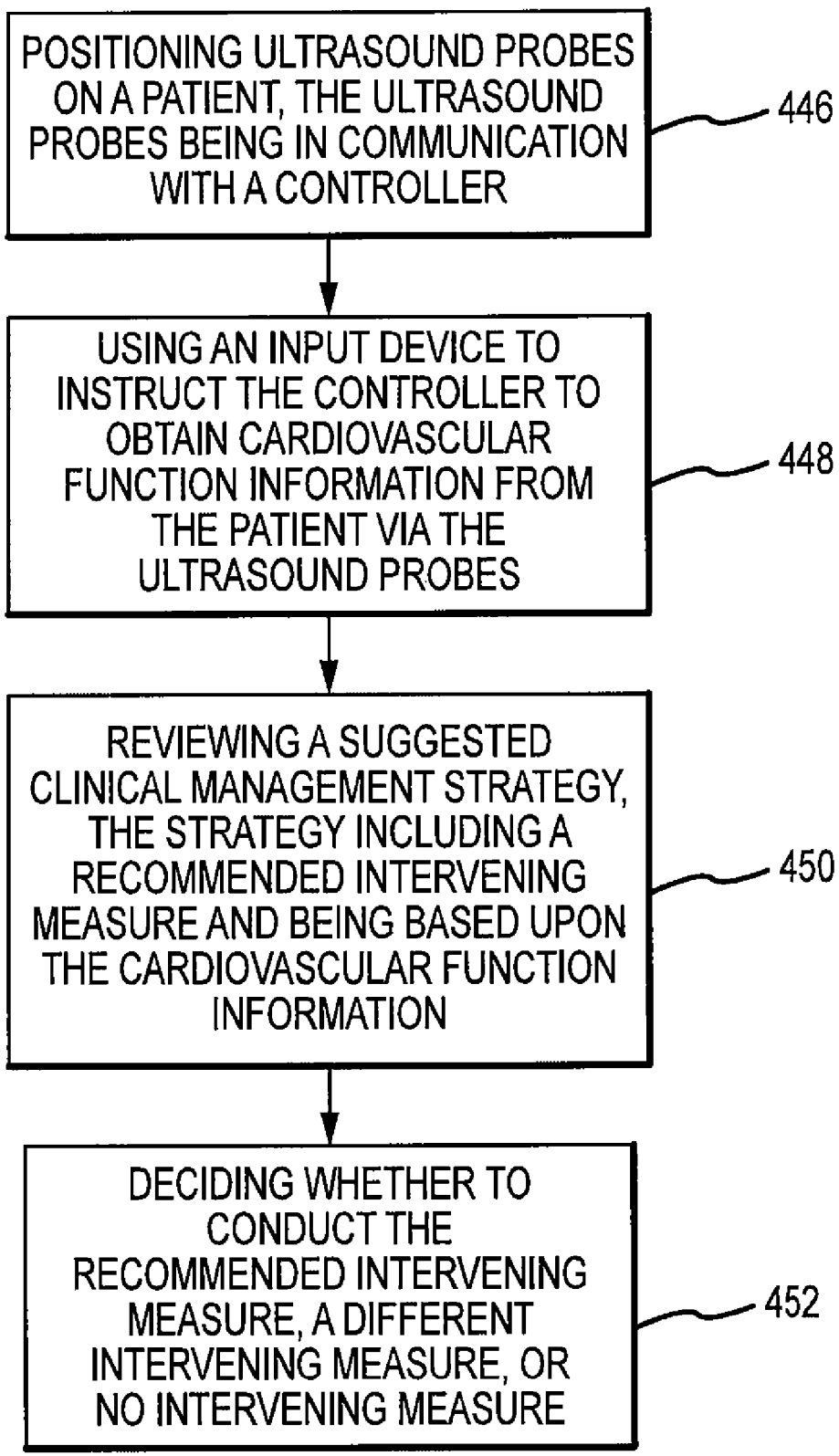
FIG. 41 is a chart showing a method of managing a patient.

Referring to FIG. 41, a method is shown including, at box 446, positioning ultrasound probes on a patient, the ultrasound probes being in communication with a controller, at box 448, using an input device to instruct the controller to obtain cardiovascular function information from the patient via the ultrasound probes, at box 450, reviewing a suggested clinical management strategy, the strategy including a recommended intervening measure and being based upon the ultrasound information, and at box 452, deciding whether to conduct the recommended intervening measure, a different intervening measure, or no intervening measure.

Figure 42:
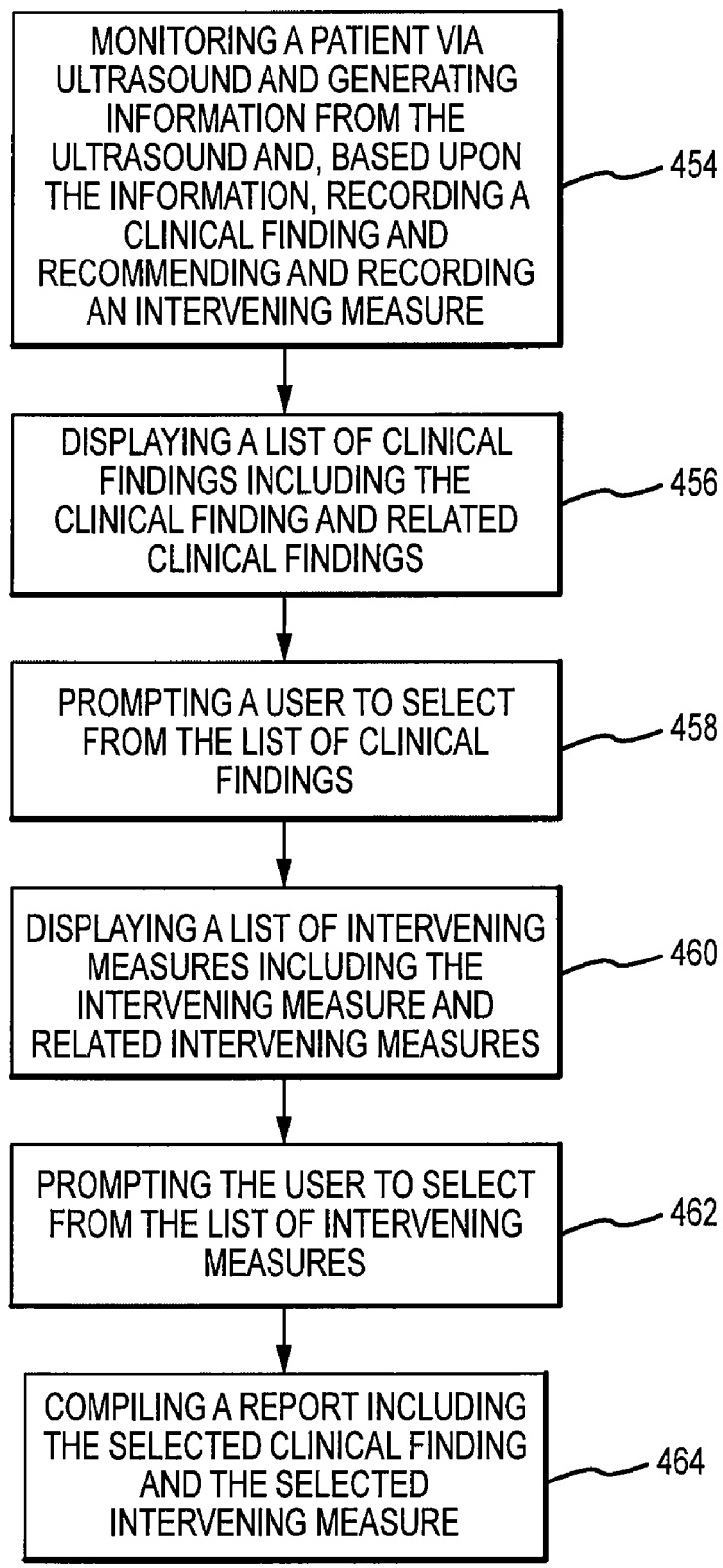
FIG. 42 is a chart showing a method of monitoring a patient.

Referring to FIG. 42, a method is shown including, at box 454, monitoring a patient via ultrasound and generating information with the ultrasound and based upon the information, recording a clinical finding and recommending and recording an intervening measure, at box 456, displaying a list of clinical findings including the clinical finding and related clinical findings, at box 458, prompting a user to select from the list of clinical findings, at box 460, displaying a list of intervening measures including the intervening measure and related intervening measures, at box 462, prompting the user to select from the list of intervening measures, and at box 464, compiling a report including the selected clinical finding and the selected intervening measure.

While the term provider has been used throughout the specification, it is to be understood that this is not limited to a licensed medical doctor, physicians assistant, nurse practitioner, and the like. Instead, provider can by any user of the system. Preferably, the provider is someone working under the guidance of a licensed practitioner and who understands cardiovascular function so as to provide suitable input to the system.

Additionally, while the phrase black and white has been used with reference to certain ultrasound images, it is to be understood that black and white means a non-color image. That is, an image that does not accurately depict the colors of the displayed elements, but rather displays similar but varying tones of several elements to make them distinguishable from one another. For example, black and white, sepia, orange, or green colors may be included within the black and white description.

Additionally, the categories of cardiovascular determinants are not to be limited to those categories disclose. More or less precise categories could be used and the image clip databases and categories can be adjusted accordingly. For example, with respect to contractile function, rather than using hyperdynamic, normal, moderately reduced, and severely reduced as categories, the categories could instead be normal and abnormal. The contractile function image clip database can be adjusted to include normal clips and abnormal clips and to include only two categories in lieu of four. This holds true for all of the image clip databases and the associated categories.

Although the present invention has been described with a certain degree of particularity, it is understood the disclosure has been made by way of example, and changes in detail or structure may be made without departing from the spirit of the invention as defined in the appended claims.

What is claimed is:

1. A method of presenting a clinical management strategy for a patient, the method comprising:
    obtaining ultrasound information regarding a condition of the patient from an ultrasound probe, the ultrasound information including cardiovascular function information about the patient;
    communicating the ultrasound information to a controller in communication with the ultrasound probe;
    employing the controller to develop from the ultrasound information a determinant reflecting the condition of the patient;
    developing the clinical management strategy with the controller by determining a status of cardiovascular function and selecting a strategy based on the status of cardiovascular function, wherein determining the status of the cardiovascular function includes: determining a cardiac output status; determining a filling pressure status; and determining a systolic blood pressure status; and
    providing on an output device in communication with the controller the clinical management strategy based on the determinant.

2. The method of claim 1, wherein obtaining ultrasound information further comprises selecting an ultrasound probe mode from a plurality of ultrasound probe modes based upon a type of ultrasound information desired.

3. The method of claim 2, wherein the plurality of ultrasound probe modes includes at least one of a 2D image, a color Doppler image, or a spectral Doppler image.

4. The method of claim 2, further comprising selecting another ultrasound probe mode from the plurality of ultrasound probe modes based upon the type of ultrasound information desired.

5. The method of claim 1, wherein obtaining ultrasound information further comprises adjusting the ultrasound probe to an ultrasound probe view, the adjusting being based on a position of the ultrasound probe on the patient and suitable ultrasound probe views available from that position.

6. The method of claim 5, wherein the ultrasound probe is positioned in a cardiovascular window and the suitable ultrasound probe views include a plurality of available cross-sectional views of a cardiovascular system.

7. The method of claim 5, further comprising adjusting the ultrasound probe to another ultrasound probe view, the adjusting being based on the position of the ultrasound probe on the patient and the suitable ultrasound probe views available from that position.

8. The method of claim 1, wherein obtaining ultrasound information further comprises selecting the ultrasound probe from a plurality of ultrasound probes positioned on the patient, the selection being based on ultrasound information available from a respective position.

9. The method of claim 8, further comprising selecting another ultrasound probe from the plurality of ultrasound probes positioned on the patient, the selection being based on information available from another respective position.

10. The method of claim 1, wherein employing the controller to develop a determinant includes determining a category for the cardiac output status or filling pressure status.

11. The method of claim 1, wherein determining the status of the cardiovascular function includes comparing a respective value to a normal value or range of values for at least one of the cardiac output status, the filling pressure status or the systolic blood pressure status.

12. The method of claim 1, wherein the ultrasound probe is configured for temporary attachment to the patient.

13. A method of developing a cardiovascular determinant of a patient, the method comprising:
    receiving ultrasound information from a patient interface, the patient interface being adapted to obtain ultrasound information related to cardiovascular function status of the patient, the ultrasound information including a captured ultrasound image clip acquired by the patient interface, the captured ultrasound image clip being reflective of a cardiovascular determinant;
    processing the ultrasound information to determine the cardiovascular function status of the patient, the processing including running an image recognition algorithm;

comparing the captured ultrasound image clip to stored ultrasound image clips of an ultrasound image clip database by determining which stored ultrasound image clip or clips the captured ultrasound image clip most closely resembles, the stored ultrasound image clips each reflecting a previously determined category related to the cardiovascular determinant;

categorizing the captured ultrasound image clip; and sending the status to a clinical management module for the development of a clinical strategy.

14. The method of claim 13, wherein categorizing the captured ultrasound image clip includes assigning a category based on the category of the stored ultrasound image clip or clips that the captured ultrasound image clip most closely resembles.

15. A method of suggesting a clinical management strategy, the method comprising:

comparing a first order data point associated with ultrasound information to a plurality of categories, the first order data point including filling pressure and the plurality of categories including normal and elevated;

comparing another first order data point associated with ultrasound information to a respective plurality of categories, the another first order data point including cardiac output and the respective plurality of categories including low and normal;

assigning a category from the plurality of categories to the first order data point based on which category of the plurality of categories the first order data point falls;

selecting a recommended intervening measure based on the assigned category, wherein, when the cardiac output is low and the filling pressure is elevated, selecting the recommended intervening measure includes selecting a reduction in afterload and a reduction in preload; and presenting the recommended intervening measure on a display.

16. A method of suggesting a clinical management strategy, the method comprising:

comparing a first order data point associated with ultrasound information to a plurality of categories, the first order data point including filling pressure and the plurality of categories including normal and elevated;

comparing another first order data point associated with ultrasound information to a respective plurality of categories, the another first order data point including cardiac output and the respective plurality of categories including low and normal;

assigning a category from the plurality of categories to the first order data point based on which category of the plurality of categories the first order data point falls;

selecting a recommended intervening measure based on the assigned category, wherein, when the cardiac output is low and the filling pressure is normal, selecting an intervening measure includes selecting a reduction in afterload and selecting to maintain the preload; and presenting the recommended intervening measure on a display.

17. The method of claim 15, further comprising:

comparing a second order data point to a second respective plurality of categories, wherein the second order data point is associated with ultrasound information; and assigning a second category from the second respective plurality of categories to the second order data point based on which category of the second respective plurality of categories the second order data point falls;

wherein, selecting a recommended intervening measure is additionally based on the second category.

18. The method of claim 17, wherein the second order data point relates to valvular function.

19. The method of claim 17, wherein the second order data point relates to valvular stenosis.

20. The method of claim 16, further comprising:

comparing a second order data point to a second respective plurality of categories, wherein the second order data point is associated with ultrasound information; and assigning a second category from the second respective plurality of categories to the second order data point based on which category of the second respective plurality of categories the second order data point falls;

wherein, selecting a recommended intervening measure is additionally based on the second category.

21. The method of claim 20, wherein the second order data point relates to valvular function.

22. The method of claim 20, wherein the second order data point relates to valvular stenosis.

* * * * *